United States Patent
Modak et al.

(10) Patent No.: US 10,542,760 B2
(45) Date of Patent: Jan. 28, 2020

(54) SKIN AND SURFACE DISINFECTANT COMPOSITIONS CONTAINING BOTANICALS

(71) Applicants: Shanta M. Modak, Riveredge, NJ (US); Nayana Baiju, New York, NY (US); Lauserpina A. Caraos, Hollis, NY (US)

(72) Inventors: Shanta M. Modak, Riveredge, NJ (US); Nayana Baiju, New York, NY (US); Lauserpina A. Caraos, Hollis, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/278,826

(22) Filed: Sep. 28, 2016

(65) Prior Publication Data

US 2017/0079282 A1   Mar. 23, 2017

Related U.S. Application Data

(63) Continuation of application No. 12/134,918, filed on Jun. 6, 2008, now Pat. No. 9,511,040, which is a continuation-in-part of application No. 12/016,788, filed on Jan. 18, 2008, now abandoned.

(60) Provisional application No. 60/953,654, filed on Aug. 2, 2007, provisional application No. 60/945,288, filed on Jun. 20, 2007.

(51) Int. Cl.
| | |
|---|---|
| A01N 65/36 | (2009.01) |
| A01N 37/02 | (2006.01) |
| A01N 31/02 | (2006.01) |
| A01N 65/22 | (2009.01) |
| A61K 8/97 | (2017.01) |
| A61K 8/36 | (2006.01) |
| A61K 8/34 | (2006.01) |
| A61K 36/53 | (2006.01) |
| A61K 36/752 | (2006.01) |
| A61K 31/19 | (2006.01) |
| A61K 31/045 | (2006.01) |
| A61Q 5/02 | (2006.01) |
| A61Q 5/12 | (2006.01) |
| A61Q 19/00 | (2006.01) |
| A61Q 17/04 | (2006.01) |
| C11D 3/48 | (2006.01) |
| C11D 17/00 | (2006.01) |
| A61K 8/365 | (2006.01) |
| A61K 8/92 | (2006.01) |
| A61Q 15/00 | (2006.01) |
| A61Q 17/00 | (2006.01) |
| A61K 31/16 | (2006.01) |
| A61Q 11/02 | (2006.01) |

(52) U.S. Cl.
CPC ............ *A01N 65/36* (2013.01); *A01N 31/02* (2013.01); *A01N 37/02* (2013.01); *A01N 65/22* (2013.01); *A61K 8/34* (2013.01); *A61K 8/345* (2013.01); *A61K 8/36* (2013.01); *A61K 8/365* (2013.01); *A61K 8/922* (2013.01); *A61K 8/97* (2013.01); *A61K 31/045* (2013.01); *A61K 31/16* (2013.01); *A61K 31/19* (2013.01); *A61K 36/53* (2013.01); *A61K 36/752* (2013.01); *A61Q 5/02* (2013.01); *A61Q 5/12* (2013.01); *A61Q 11/02* (2013.01); *A61Q 15/00* (2013.01); *A61Q 17/005* (2013.01); *A61Q 17/04* (2013.01); *A61Q 19/00* (2013.01); *A61Q 19/002* (2013.01); *C11D 3/48* (2013.01); *C11D 17/0047* (2013.01)

(58) Field of Classification Search
None
See application file for complete search history.

(56) References Cited

U.S. PATENT DOCUMENTS

| | | | |
|---|---|---|---|
| 4,022,605 A | 5/1977 | Konya et al. | |
| 4,049,802 A | 9/1977 | Fox, Jr. | |
| 4,330,531 A | 5/1982 | Alliger | |
| 4,404,197 A | 9/1983 | Fox, Jr. et al. | |

(Continued)

FOREIGN PATENT DOCUMENTS

| | | |
|---|---|---|
| CH | 654327 A5 | 2/1986 |
| DE | 202004018623 U1 | 4/2005 |

(Continued)

OTHER PUBLICATIONS

Anand, P., et al., "Biological activities of curcumin and its analogues (Congeners) made by man and Mother Nature," Biochemical Pharmacology 2008, pp. 1590-1611, vol. 76, No. 11, DOI: 10.1016/j.bcp.2008.08.008, Publisher: Elsevier Inc.

(Continued)

*Primary Examiner* — Michael P Cohen
(74) *Attorney, Agent, or Firm* — Beusse Wolter Sanks & Maire; Timothy H. Van Dyke

(57) ABSTRACT

The present invention relates to a skin or surface disinfectant composition with broad spectrum antimicrobial activity comprising one or more essential oil (and/or one or more component thereof) and one or more fruit acid. The compositions of the invention may be used as non-toxic alternatives to conventional disinfectants or may be added to other antimicrobial agents to enhance their activity. The invention provides effective alternatives to harsher products which may be particularly useful in personal care and household products and where children and/or pet exposure may be a concern.

8 Claims, No Drawings

(56) References Cited

U.S. PATENT DOCUMENTS

| | | |
|---|---|---|
| 4,563,485 A | 1/1986 | Fox, Jr. et al. |
| 4,579,731 A | 4/1986 | Fox, Jr. et al. |
| 4,581,028 A | 4/1986 | Fox, Jr. et al. |
| 4,612,337 A | 9/1986 | Fox, Jr. et al. |
| 4,723,950 A | 2/1988 | Lee |
| 4,859,359 A | 8/1989 | DeMatteo et al. |
| 4,867,898 A | 9/1989 | Spaulding et al. |
| 4,956,354 A | 9/1990 | Gutierrez |
| 4,975,217 A | 12/1990 | Brown-Skrobot et al. |
| 5,019,096 A | 5/1991 | Fox, Jr. et al. |
| 5,033,488 A | 7/1991 | Curtis et al. |
| 5,073,366 A | 12/1991 | Beck |
| 5,091,442 A | 2/1992 | Milner |
| 5,100,652 A | 3/1992 | Kross et al. |
| 5,135,747 A | 8/1992 | Faryniarz et al. |
| 5,180,605 A | 1/1993 | Milner |
| 5,200,194 A | 4/1993 | Edgren et al. |
| 5,209,251 A | 5/1993 | Curtis et al. |
| 5,261,421 A | 11/1993 | Milner |
| 5,310,546 A | 5/1994 | Douglas |
| 5,334,588 A | 8/1994 | Fox, Jr. et al. |
| 5,567,495 A | 10/1996 | Modak et al. |
| 5,614,538 A | 3/1997 | Nelson, Jr. |
| 5,616,338 A | 4/1997 | Fox, Jr. et al. |
| 5,772,640 A | 6/1998 | Modak et al. |
| 5,854,266 A | 12/1998 | Nelson, Jr. |
| 5,866,527 A | 2/1999 | Mertens |
| 5,891,422 A | 4/1999 | Pan et al. |
| 5,968,539 A | 10/1999 | Beerse et al. |
| 5,985,819 A | 11/1999 | Lu et al. |
| 5,985,918 A | 11/1999 | Modak et al. |
| 6,075,056 A | 6/2000 | Quigley, Jr. et al. |
| 6,083,208 A | 7/2000 | Modak et al. |
| 6,106,505 A | 8/2000 | Modak et al. |
| 6,120,758 A | 9/2000 | Siddiqui et al. |
| 6,258,368 B1 * | 7/2001 | Beerse ............... A61K 8/0208 424/401 |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,348,501 B1 | 2/2002 | Holt et al. |
| 6,397,224 B1 | 5/2002 | Zubeldia et al. |
| 6,420,326 B1 | 7/2002 | Maile et al. |
| 6,451,748 B1 | 9/2002 | Taylor et al. |
| 6,537,955 B1 | 3/2003 | Raso et al. |
| 6,582,719 B2 | 6/2003 | Modak et al. |
| 6,616,922 B2 | 9/2003 | Taylor et al. |
| 6,630,163 B1 | 10/2003 | Murad |
| 6,632,784 B2 | 10/2003 | Massaux et al. |
| 6,635,676 B2 | 10/2003 | Baker, Jr. et al. |
| 6,696,399 B1 | 2/2004 | Chernin et al. |
| 6,699,825 B2 | 3/2004 | Rees et al. |
| 6,716,883 B1 | 4/2004 | Casper et al. |
| 6,753,305 B2 | 6/2004 | Raso et al. |
| 6,858,317 B2 | 2/2005 | Aamodt et al. |
| 6,921,745 B2 | 7/2005 | Yamada et al. |
| 6,951,833 B2 | 10/2005 | O'Neil |
| 6,969,522 B2 | 11/2005 | Bessette et al. |
| 7,247,295 B2 | 7/2007 | Schmaus et al. |
| 7,435,429 B2 | 10/2008 | Modak et al. |
| 7,563,461 B2 | 7/2009 | Modak et al. |
| 7,563,462 B2 | 7/2009 | Modak et al. |
| 7,572,469 B2 | 8/2009 | Santo et al. |
| 7,745,425 B2 | 6/2010 | Modak et al. |
| 7,871,649 B2 | 1/2011 | Modak et al. |
| 7,985,773 B2 | 7/2011 | Greten et al. |
| 2001/0010016 A1 | 7/2001 | Modak et al. |
| 2001/0024661 A1 | 9/2001 | Modak et al. |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0113388 A1 | 6/2003 | Phan |
| 2003/0168077 A1 | 9/2003 | Brown et al. |
| 2003/0180233 A1 | 9/2003 | Anderson et al. |
| 2003/0195263 A1 | 10/2003 | Schmaus et al. |
| 2003/0213168 A1 | 11/2003 | Hesse et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0247685 A1 | 12/2004 | Modak et al. |
| 2004/0253275 A1 | 12/2004 | Eini et al. |
| 2005/0019431 A1 * | 1/2005 | Modak ............... A01N 33/12 424/736 |
| 2005/0026802 A1 | 2/2005 | Kilkenny et al. |
| 2005/0048139 A1 | 3/2005 | Modak et al. |
| 2005/0063939 A1 | 3/2005 | Ameer et al. |
| 2005/0187124 A1 | 8/2005 | Li et al. |
| 2005/0222276 A1 * | 10/2005 | Schmaus ............ A01N 31/02 514/738 |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata et al. |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2007/0286813 A1 | 12/2007 | Toutounghi |
| 2008/0008729 A1 | 1/2008 | Swaine et al. |
| 2008/0038219 A1 | 2/2008 | Mosbaugh et al. |
| 2008/0063607 A1 | 3/2008 | Tamarkin et al. |
| 2008/0166314 A1 | 7/2008 | Jochim et al. |
| 2008/0226568 A1 | 9/2008 | Rozsa et al. |
| 2008/0234173 A1 | 9/2008 | Warr et al. |
| 2008/0253976 A1 | 10/2008 | Scott et al. |
| 2008/0260708 A1 | 10/2008 | Hall |
| 2008/0299220 A1 | 12/2008 | Tamarkin et al. |
| 2008/0311231 A1 | 12/2008 | Modak et al. |
| 2008/0317737 A1 | 12/2008 | Patel et al. |
| 2008/0318784 A1 | 12/2008 | Koo et al. |
| 2009/0004122 A1 | 1/2009 | Modak et al. |
| 2009/0028751 A1 | 1/2009 | Robbins |
| 2009/0029961 A1 | 1/2009 | Modak et al. |
| 2009/0035228 A1 | 2/2009 | Modak et al. |
| 2009/0068255 A1 | 3/2009 | Yu et al. |
| 2009/0088358 A1 | 4/2009 | Roso et al. |
| 2009/0165812 A1 | 7/2009 | Resnick et al. |
| 2009/0175806 A1 | 7/2009 | Modak et al. |
| 2009/0191288 A1 | 7/2009 | Squires et al. |
| 2009/0300864 A1 | 12/2009 | Adkins et al. |
| 2010/0034871 A1 | 2/2010 | Mikkelsen et al. |
| 2010/0093595 A1 | 4/2010 | Holzhauer et al. |
| 2010/0140368 A1 | 6/2010 | De Lame et al. |
| 2010/0172847 A1 | 7/2010 | Modak et al. |
| 2010/0172848 A1 | 7/2010 | Modak et al. |
| 2010/0183524 A1 | 7/2010 | Zielinski et al. |
| 2010/0196494 A1 | 8/2010 | VanBeek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070376 A1 | 3/2011 | Wales et al. |
| 2011/0142899 A1 | 6/2011 | Lagaron Abello et al. |
| 2012/0100231 A1 | 4/2012 | Perla et al. |
| 2012/0129950 A1 | 5/2012 | Macinga et al. |
| 2012/0171156 A1 | 7/2012 | Basketter et al. |
| 2012/0201902 A1 | 8/2012 | Modak et al. |
| 2012/0207862 A1 | 8/2012 | Morre et al. |
| 2013/0230609 A1 | 9/2013 | Modak et al. |
| 2014/0079819 A1 | 3/2014 | Debaun et al. |

(56) References Cited

U.S. PATENT DOCUMENTS

| | | |
|---|---|---|
| 2014/0178447 A1 | 6/2014 | Modak et al. |
| 2014/0242198 A1 | 8/2014 | Modak et al. |
| 2014/0243417 A1 | 8/2014 | Modak et al. |
| 2014/0287072 A1 | 9/2014 | Modak et al. |
| 2014/0322147 A1 | 10/2014 | Modak et al. |

FOREIGN PATENT DOCUMENTS

| | | | |
|---|---|---|---|
| DE | 202008002718 U1 | 7/2009 | |
| EP | 0054205 A1 | 6/1982 | |
| EP | 0106266 A2 | 4/1984 | |
| EP | 0231080 A1 | 8/1987 | |
| EP | 1108419 A1 | 6/2001 | |
| EP | 1146112 A1 | 10/2001 | |
| EP | 1206933 A1 | 5/2002 | |
| EP | 1288285 A1 | 3/2003 | |
| FR | 2771632 A1 | 6/1999 | |
| FR | 2874928 A3 | 3/2010 | |
| GB | 1060447 | 3/1967 | |
| JP | 1997-323910 A | 12/1997 | |
| JP | 2002-193717 A | 7/2002 | |
| JP | 2002-370958 A | 12/2002 | |
| JP | 2004-217615 A | 8/2004 | |
| JP | 04250331 A | 9/2004 | |
| JP | 2004-277554 A | 10/2004 | |
| JP | 2004-322078 | 11/2004 | |
| JP | 2006-225289 A | 8/2006 | |
| JP | 2007-291049 A | 11/2007 | |
| JP | 2010-83806 A | 4/2010 | |
| JP | 2010-184987 A | 8/2010 | |
| KR | 10-2004-077206 | 9/2004 | |
| SU | 513676 A1 | 5/1976 | |
| WO | 84/04456 A1 | 11/1984 | |
| WO | 85/01208 A1 | 3/1985 | |
| WO | 89/06962 A1 | 8/1989 | |
| WO | 92/04029 A1 | 3/1992 | |
| WO | 93/02717 A1 | 2/1993 | |
| WO | 98/51273 A1 | 11/1998 | |
| WO | 99/22718 A1 | 5/1999 | |
| WO | 00/65011 A1 | 11/2000 | |
| WO | 01/72262 A2 | 10/2001 | |
| WO | 01/91555 A2 | 12/2001 | |
| WO | 02/22060 A1 | 3/2002 | |
| WO | 03/000303 A1 | 1/2003 | |
| WO | 03/018498 A1 | 3/2003 | |
| WO | 03/018743 A2 | 3/2003 | |
| WO | 03/077856 A2 | 9/2003 | |
| WO | 03/078367 A2 | 9/2003 | |
| WO | 2004/004631 A2 | 1/2004 | |
| WO | 2004/014416 A1 | 2/2004 | |
| WO | 2006/010269 A1 | 2/2006 | |
| WO | 2006/023349 A1 | 3/2006 | |
| WO | 2006/099359 A2 | 9/2006 | |
| WO | 2007/069214 A2 | 6/2007 | |
| WO | 2007/071089 A1 | 6/2007 | |
| WO | WO 2007070795 A2 * | 6/2007 | ............ A61K 8/345 |
| WO | 2007/077573 A1 | 7/2007 | |
| WO | 2007/095041 A2 | 8/2007 | |
| WO | 2007/101848 A1 | 9/2007 | |
| WO | 2007/123790 A1 | 11/2007 | |
| WO | 2007/126651 A2 | 11/2007 | |
| WO | 2008/031087 A1 | 3/2008 | |
| WO | 2008/042197 A1 | 4/2008 | |
| WO | 2008/061187 A1 | 5/2008 | |
| WO | 2008/119841 A2 | 10/2008 | |
| WO | WO-2008135085 A1 * | 11/2008 | ............ A61K 8/345 |
| WO | 2008/154395 A1 | 12/2008 | |
| WO | 2008/157847 A1 | 12/2008 | |
| WO | 2009/062746 A2 | 3/2009 | |
| WO | 2009/049208 A1 | 4/2009 | |
| WO | 2010/091415 A1 | 8/2010 | |
| WO | 2010/119369 A2 | 10/2010 | |
| WO | 2011/002929 A1 | 1/2011 | |
| WO | 2011/151835 A1 | 12/2011 | |
| WO | 2012/017349 A2 | 2/2012 | |
| WO | 2012/051204 A2 | 4/2012 | |
| WO | 2013/066403 A1 | 5/2013 | |
| WO | 2013/103556 A1 | 7/2013 | |
| WO | 2014/092999 A1 | 6/2014 | |

OTHER PUBLICATIONS

Ayliffe, G.A.J., et al., "Hand disinfection: A comparison of various agents in laboratory and ward studies," Journal of Hospital Infection 1988, pp. 226-243, vol. 11.

Bagamboula, C.F, et al., "Inhibitory effect of thyme and basil essential oils, carvacrol, thymol, estragol, linalool and p-cymene towards Shigella sonnei and S. flexneri," Food Microbiology 2004, pp. 33-42, vol. 21.

Baiju, N., et al., "Development of a novel surface disinfectant composition containing essential oils and fruit acid against nosocomial pathogens commonly associated with environmental surfaces," International Journal of Essential Oil Therapeutics 200, pp. 9-14, vol. 2.

Bettini, M., "Purification of Orange Peel Oil and Oil Phase by Vacuum Distillation," Functional Food Ingredients and Nutraceuticals, Processing Technologies 2006, pp. 157-172, Editor: John Shi, Publisher: CRC Press.

Bezic, N., et al., "Composition and antimicrobial activity of Achillea clavennae L. essential oil." Phytother. Res. 2003, pp. 1037-1040, vol. 17.

Bion, "Acne—Acne Treatment Products," http://www.bion-research.com/acne_treatment_products.htm, downloaded on Mar. 3, 2008, pp. 1-3.

Bion, "Moderate to Severe Acne," http://www.bion- research.com/moderate-to- severe acne.htm, downloaded on Mar. 3, 2008, pp. 1-5.

Biosecur Lab, "Biosecur Product Line Receives Self-Affirmed Gras Status for Use as an antioxidant and Nutrient Supplement", News Release dated Mar. 8, 2011, pp. 1-2.

Bio Source Naturals, "Lemongrass Essential Oil: (*Cymbopogon citratus*)," http://www.biosourcenaturals.com/lemongrass-essential-oil.htm, retrieved on Apr. 5, 2015, pp. 1-2.

Brehm-Stecher, B.F. and Jonson, E.A., "Sensitization of *Staphylococcus aureus* and *Escherichia coli* to antibiotics by the sesquiterpenoids nerolidol, farnesol, bisabolol, and apritone," Antimicrobial Agents and Chemotherapy 2003, pp. 3357-3360, vol. 47, No. 10.

Cancio, L.C., "Burn wound infections," Surgical Treatment: Evidence-Based and Problem-Oriented 2001, pp. 1-20, Editors: Holzheimer, R.G. and Mannick, J.A.

Chang, S., et al., "Resources and bioactive substances from Taiwania (Taiwania cryptomerioides)," J. Wood Sci 2003, pp. 1-4, vol. 49, Publisher: The Japan Wood Research Society.

Chemical Book, "8015-73-4(Basil oil) Product Description," http://www.chemicalbook.com/ChemicalProductProperty_US_CB3405198.aspx, retrieved on Jul. 1, 2015, pp. 1-2.

Choudhary, V.R., et al., "Solvent-free selective oxidation of benzyl alcohol and benzaldehyde by tert-butyl hydroperoxide using Mn04-exchanged Mg—Al-hydrotalcite catalsysts," Catalysis Letters 2003, pp. 229-233, vol. 86, No. 4.

Collins, D.A., "A review of alternatives to organophosphorus compounds for the control of storage mites,"Journal of Stored Products Research 2006, pp. 395-426, vol. 42, Publisher: Elsevier Ltd.

Cowan., M. M., "Plant product as antimicrobial agents", Clinical Microbiology Reviews 1999, pp. 564-582, vol. 12, No. 4, Publisher: American Society for Microbiology.

Daily Med, "Antiseptic Skin Cleanser—chlorhexidine gluconate liquid, Drug Label Information," https://dailymed.nlm.nih.gov/dailymed/drugInfo.cfm?setid=5577ecbb-cf2c-45e1-a0fb-17df . . . , updated on Sep. 2012, retrieved on Jun. 24, 2016, pp. 1-2.

De Abreu Gonzaga, W., et al., "Composition and antibacterial activity of the essential oils from Zanthoxylum rhoifolium," Planta Med. 2003, pp. 773-775, vol. 69.

El-Zemity, S.R. and Ahmed, S.M., et al., "Antifungal activity of some essential oils and their major chemical constituents against some phytopathogenic fungi," Journal of Pest Control and Enviromental Science 2005, pp. 61-72, vol. 13, No. 1.

(56) References Cited

OTHER PUBLICATIONS

EPO: Office Action, European Patent Application No. 10794733.5, dated Dec. 2, 2014, pp. 1-9.
EPO: Supplementary Partial European Search Report, European Patent Application No. 12846062.3, dated Aug. 12, 2015, pp. 1-8.
EPO: Extended Search Report, European Patent Application No. 08780771.5, dated Jan. 2, 2013, pp. 1-6.
Esoteric Oils, "Lemongrass essential oil information," http/www.essentialoils.co.za/essential-oils/lemongrass.htm, downloaded on Jul. 15, 2012, p. 1.
Esoteric Oil, "Orange essential oil (sweet information)," http://www.essentialoils.co.za/essential-oils/orange.htm, retrieved on Jul. 15, 2012, p. 1.
Fang, C., et al., "Prospective clinical study of Hydron, a synthetic dressing, in delivery of an antimicrobial drug to second-degree burns," J Burn Care Rehabil. 1987, pp. 206-209, vol. 8, No. 3.
Fox, C.L., et al., "Comparative evaluation of zinc sulfadiazine and silver sulfadiazine in burn wound infection," J Burn Care Rehabil. 1990, pp. 112-117, vol. 11, No. 2.
Gaonkar, T.A., et al., "In vivo efficacy of an alcohol-based surgical hand disinfectant containing a synergistic combination of ethylhexylglycerin and preservatives," Journal of Hospital Injection 2006, pp. 412-417, vol. 63.
Gaonkar, T.A., et al., "An alcohol hand rub containing a synergistic combination of an emollient and preservatives: prolonged activity against transient pathogens", Journal of Hospital Injections 2005, pp. 12-18, vol. 59.
Garcia, C.C., et al., "Virucidal activity of essential oils from aromatic plants of San Luis, Argentina," Phytother. Res. 2003, pp. 1073-1075, vol. 19, No. 9.
Gemeda, N., "Effect of essential oils on aspergillus spore germination, growth and mycotoxin production: a potential source of botanical food preservative", Asian Pacific Journal of Tropical Biomedicine 2014, pp. S373-S381, vol. 4 (Suppl).
Gershon, H. and Shanks, L., "Antifungal Properties of n-Alkanols, a, w-n-Alkanedoils, and w-Chloro-a-alkanols", J Pharm. Sci. 1980, pp. 381-384, vol. 64, No. 4.
Goren, A.C., et al., "Analysis of essential oil of Coridothymus capitatus (L.) and its antibacterial and antifungal activity," Z. Naturforsch. 2003, pp. 687-690, vol. 58, No. 9-10.
Hajhashemi, V., et al., "Anti-inflammatory and analgesic properties of the leaf extracts and essential oil of Lavandula angustifolia Mill." J. Ethnopharmacol. 2003, pp. 67-71, vol. 89.
Hazan, R., et al., "Benzoic Acid, a Weak Organic Acid Food Preservative, Exerts Specific Effects on Intracellular Membrane Trafficking Pathways in Saccharomyces cerevisiae," Appl. Environ. Microbial. 2004, pp. 4449-4457, vol. 70, No. 8.
ISA/US: International Search Report and Written Opinion, International Patent Application No. PCT/US2013/071731, dated Feb. 12, 2014, pp. 1-11.
ISA/US: International Search Report and Written Opinion, International Patent Application No. PCT/US2012/037135, dated Oct. 16, 2012, pp. 1-13.
ISA/US: International Search Report and Written Opinion, International Patent Application No. PCT/US2012/052793, dated Nov. 19, 2012, pp. 1-14.
ISA/US: International Search Report and Written Opinion, International Patent Application No. PCT/US2012/63013, dated Jan. 4, 2013; pp. 1-8.
ISA/US: International Search Report and Written Opinion, International Patent Application No. PCT/US15/62454, dated Feb. 9, 2016, pp. 1-12.
ISA/US: International Search Report and Written Opinion, International Patent Application No. PCT/US14/29486, dated Oct. 10, 2014, pp. 1-14.
JPO: Rejection, Japanese Patent Application No. 2014-539926, dated Jan. 19, 2016, 17 pages.

Judzentiene, A., et al., "Characterisitcs of essential oil composition in the needles of young Scots pine (Pinus sylvestris L.) stands growing along an aerial ammonia gradient," CHEMIJA 2006, pp. 67-73, vol. 17, No. 4.
Keeven, J., et al., "Evaluating the preservative effectiveness of RGP lens care solutions," CLAO J. 1995, pp. 238-241, vol. 21, No. 4.
Klaric, M.S., et al., "Antifungal activity of thyme (Thymus vulgaris L.) essential oil and thymol against moulds from damp dwellings," Letters in Applied Microbiology 2007, pp. 36-42, vol. 44, No. 1.
Komthong, P., et al., "Ascending bubble extraction of terpenes from freshly squeezed orange juice", Food Research International 2006, pp. 53-58, vol. 39.
Kumar, A., et al., "Assessment of Thymus vulgaris L. essential oil as a safe botanical preservative against post harvest fungal infestation of food commodities", Innovative Food Science and Emerging Technologies 2008, pp. 575-580, vol. 9, No. 4.
Kurita, N. and Koike, S., "Synergistic Antimicrobial Effect of Ethanol, Sodium Chloride, Acetic Acid and Essential Oil Components," Agricultural Biology Chemistry 1983, pp. 67-75, vol. 47, No. 1.
Mercola.com, "Lemongrass Oil: Lighten Up Your Mood with This All-Around Oil," http://articles.mercola.com/herbal-oils/lemongrass-oil.aspx, printed on Mar. 26, 2015, pp. 1-4.
Mintel Global New Products Database 2008, "Antibacterial Wet Wipes," retrieved from the Internet: URL:www.gnQd.com, retrieved on Sep. 24, 2013, pp. 1-2.
Mintel Global New Products Database 2010, "Sheer Moisturizer Hand Sanitizer", retrieved from the Internet: URL:www.gn.Qd.com on Aug. 24, 2013, pp. 1-4.
Morganics, "Skin Care," www.morganics.com/store/page8.html, Morganics, retrieved on Jul. 1, 2015, p. 1.
Nazer, A.I., et al., "Combinations of food antimicrobials at low levels to inhibit the growth of Salmonella sv. Typhimurium: a synergistic effect?," Food Microbiology 2005, pp. 391-398, vol. 22.
Nerio, L.S., et al., "Repellant activity of essential oils: A review", Biosource Technology 2010, pp. 372-378, vol. 101.
Panchatcharam, M., et al., "Curcumin improves wound healing by modulating collagen and decreasing reactive oxygen species," Molecular and Cellular Biochemistry 2006, pp. 87-96, vol. 290, Publisher: Springer.
Pommier, P., et al., "Phase III Randomized Trial of Calendula Officinalis Compared With Trolamine for the Prevention of Acute Dermatitis During Irradiation for Breast Cancer," J Clin Oncol 2004, pp. 1447-1453, vol. 22, No. 8.
Prabuseenivasan, S., et al., "In vitro antibacterial activity of some plant essential oils", BMC Complementary and Alternative Medicine 2006, pp. 1-8, vol. 6, No. 39.
Reagor, L, et al., "The Effectiveness of Processed Grapefruit-Seed Extract as an Antibacterial Agent: I. An In Vitro Agar Assay," The Journal of Alternative and Complementary Medicine 2002, pp. 325-332, vol. 8, No. 3.
Subba, M.S., et al., "Antimicrobial Action of Citrus Oils," J. Food Sci. 1967, pp. 225-227, vol. 32, No. 2.
"Table of Acids with Ka and pKa Values," Chem 1A, B, C Lab Manual and Zumdahl 6th Edition, Appendix 5, http://clas.sa.ucsb.edu/staff/Resource%20folder/Chem109ABC/Acid,%20Base%20Strength/Table%20of%20Acids%20w%20Ka s%20and%20pKas.pdf, downloaded on Sep. 28, 2015.
Tayyem, R.F., et al., "Curcumin Content of Turmeric and Curry Powders", Nutrition and Cancer 2006, pp. 126-131, vol. 55, No. 2, Publisher: Lawrence Erlbaum Associates, Inc.
The Lubrizol Corporation, "Tecophilic TPU—LifeScience Polymers," https://web.archive.org/web/20140923074123/http: 1/www.lubrizol.com/LifeScience/Products/Tecophilic.html; Sep. 23, 2014 [downloaded from internet on Jan. 12, 2016], pp. 1-2.
The Merck Index, "02322. Citral," 2011, pp. 1-2, 14th Edition, Publisher: Merck Sharp & Dohme Corp.
Valero, M. and Salmeron, M.C., "Antibacterial activity of 11 essential oils against Bacillus cereus in tyndallized carrot broth," Int. J. Food Microbial. 2003, pp. 73-81, vol. 85.
Velluti, A., et al., "Inhibitory effect of cinnamon, clove, lemongrass, oregano and palmarose essential oils on growth and fumonisin B1

(56) References Cited

OTHER PUBLICATIONS production by Fusarium proliferatum in maize grain," Int. J. Food Microbial. 2003, pp. 145-154, vol. 89.
Wilson, N.D., et al., "The quantification of citral in lemongrass and lemon oils by near-infrared spectroscopy", Journal of Pharmacy and Pharmacology 2002, pp. 1257-1263, vol. 54, Publisher: The Authors.
Zeus Quimica, S.A, "Zemea Propanediol—From Corn to Cosmetics . . . Formulate with Nature," downloaded on Jun. 24, 2015, p. 1.
Zhang, Z., et al., "Antifungal Activities of Major Tea Leaf Volatile Constituents toward Colletorichum Camelliae Massea," Journal of Agricultural and Food Chemistry 2006, pp. 3936-3940, vol. 54.
Baratta, M.T., et al., "Antimicrobial and antioxidant properties of some commercial essential oils," Flavour and Fragrance Journal 1998, pp. 235-244, vol. 13.
Block, S.S., "Disinfection, Sterilization, and Preservation; Fourth Edition," 1991, Pages Cover, 280-281 and 892, Publisher: Lea & Febiger.
Chalchat, J.C. et al, "Chemical Composition of Essential Oil of *Calendula officinalis* L. (Pot Marigold)," Flavour and Fragrance Journal 1991, pp. 189-192, vol. 6.
EPO: Extended Search Report, European Patent Application No. 12845196.0, dated Sep. 5, 2016, pp. 1-8.
EPO: Partial Supplementary Search Report, European Patent Application No. 12845196.0, dated May 17, 2016, pp. 1-6.
EPO: Supplementary Partial European Search Report, European Patent Application No. 12846062.3, dated Jan. 8, 2016, pp. 1-14.
EPO: Supplementary Search Report, European Patent Application No. 14763192.3, dated Jan. 5, 2017, pp. 1-7.
Gupta, V.K., "Third Party Observation," filed in U.S. Appl. No. 12/694,119, filed Aug. 7, 2010, pp. 1-35.
Gupta, V.K., "Third Party Observation," filed in U.S. Appl. No. 12/694,141, filed Jul. 19, 2010, pp. 1-26.
IP Australia: Patent Examination Report No. 1, Australian Patent Application No. 2012332495, dated Jun. 10, 2016, pp. 1-3.
Jabra-Rizk, M.A., et al., "Effects of Farnesol on *Staphlyococcus aureus* Biofilm Formation and Antimicrobial Suspectibility," Antimicrobial Agents and Chemotherapy 2006, pp. 1463-1469, Publisher: American Society for Microbiology.
Kupferwasser, L.I., et al., "Salicylic Acid Attenuates Virulence in Endovascular Infections by Targeting Global Regulatory Pathways in *Staphylococcus aureus*," J. Clin. Invest. 2003, pp. 222-233, vol. 112.
Kupferwasser, L.I., et al., "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects," Circulation 1999, pp. 2791-2797, vol. 99, Publisher: American Heart Association, Inc.
Minami, M., et al., "The inhibitory effect of essential oils on herpes simplex virus type-1 replication in vitro," Microbial Immunol. 2003, pp. 681-684, vol. 47, No. 9.
Nannapaneni, R., et al., "Antimicrobial activity of commercial citrus-based natural extracts against *Escherichia coli* 0157:H7 isolates and mutant strains", Foodborne Pathogens and Disease 2008, pp. 695-699, vol. 5, No. 5, Publisher: Mary Ann Liebert, Inc.
Paranagama, P.A., et al., "Fungicidal and anti-aflatoxigenic effects of the essential oil of *Cymbopogon citratus* (DC.) Stapf. (lemongrass) against Aspergillus flavus Link. isolated from stored rice," Lett. Appl. Microbial. 2003, pp. 86-90, vol. 37.
Sharma, A., "Third Party Observation," filed in Canadian Patent Application No. 2769627, Jun. 25, 2014, pp. 1-39.
Schuhmacher, S., et al., "Virucidal effect of peppermint oil on the enveloped viruses herpes simplex virus type 1 and type 2 in vitro," Phytomedicine 2003, pp. 504-510, vol. 10.
Shin, S., "Anti-Aspergillus activities of plant essential oils and their combination effects with ketoconazole or amphotericin B", Arch. Pharm. Res. 2003, pp. 389-393, vol. 26, No. 5.
Silva, J., "Analgesic and anti-inflammatory effects of essential oils of Eucalyptus," J. Ethnopharmacol. 2003, pp. 277-283, vol. 89.
Song, Q., et al., "Volatiles from Ficus hispida and their attractiveness to fig wasps", Journal of Chemical Ecology 2001, pp. 1929-1942, vol. 27, No. 10.
Watts, J. L., et al., "Evaluation of Test Dips with Excised Teats," Journal of Dairy Science 1984, pp. 2062-2065, vol. 67, Issue 9.

\* cited by examiner

SKIN AND SURFACE DISINFECTANT COMPOSITIONS CONTAINING BOTANICALS

PRIORITY CLAIMED

This application is a continuation of U.S. patent application Ser. No. 12/134,918, filed Jun. 6, 2008 which is a continuation-in-part of U.S. patent application Ser. No. 12/016,788, filed Jan. 18, 2008, which claims priority benefits to U.S. Provisional Application Ser. No. 60/953,654, filed Aug. 2, 2007, and also claims priority to U.S. Provisional Application No. 60/945,288, filed Jun. 20, 2007, all of which are hereby incorporated by reference in their entireties herein.

INTRODUCTION

The present invention relates to a skin or surface disinfectant composition with broad spectrum antimicrobial activity comprising one or more essential oil (and/or one or more component thereof) and one or more fruit acid. The compositions of the invention may be used as non-toxic alternatives to conventional disinfectants or may be combined with other antimicrobial agents to enhance their activity. The invention provides effective alternatives to harsher products, and may be particularly useful in personal care and household product applications and where children and/or pet exposure may be a concern.

BACKGROUND OF THE INVENTION

Essential oils are volatile oils obtained from plant or animal sources and are composed of complex mixtures of several constituents, such as monoterpenes and sesquiterpene hydrocarbons, monoterpene and sesquiterpene alcohols, esters, ethers, aldehydes, ketones, oxides and the like. These essential oils and their isolated constituents are frequently utilized as fragrance and flavor agents, and have been widely used in folk medicine for wound healing properties.

Scientific research has corroborated the beneficial effects of essential oils. Essential oils of eucalyptus have been found to "possess central and peripheral analgesic effects as well as neutrophil-dependent and independent anti-inflammatory activities" (Silva et al., 2003, J. Ethnopharmacol. 89(2-3); 277-283), and similar activity has been observed in essential oils from *Lavandula angustifolia* (Hajhashemi et al., 2003, J. Ethnopharmacol. 89(1):67-71). Essential oils have been demonstrated to exhibit antibacterial (Bezic et al., 2003, Phytother. Res. 17(9):1037-1040; Goren et al., 2003, Z. Naturforsch. 58(9-10):687-690; de Abreu Gonzaga et al., 2003, Planta Med. 69(8):773-775; Valero and Salmera, 2003, Int. J. Food Microbiol. 85(1-2): 73-81) and antifungal (Paranagama et al., 2003, Lett. Appl. Microbiol. 37(1):86-90; Shin, 2003, Arch. Pharm. Res. 26(5):389-393; Velluti et al., 2003, Int. J. Food Microbiol. 89:145-154) activities. Virucidal activity of essential oils has also been observed, including direct virucidal effects against Herpes simplex viruses types 1 and 2 (Garcia et al., Phytother. Res. 17(9): 1073-1075; Minami et al., 2003, Microbial Immunol. 47(a): 681-684; Schuhmacher et al., 2003, Phytomedicine 10:504-510).

United States Patent Application Publication No. 20050048139 by Modak et al., published Mar. 3, 2005, relates to topical compositions comprising an emollient solvent and an essential oil, which may further comprise additional additives, among which citric acid, glycolic acid and lactic acid are cited. It does not recognize the synergistic activity between essential oils and fruit acids nor does it disclose the concentrations of fruit acids to be used to provide a synergistic effect.

United States Patent Application Publication No. 20050019431 by Modak et al., published Jan. 27, 2005, relates to compositions comprising a quaternary ammonium compound and an essential oil (or active component thereof).

A number of patent applications relate to compositions comprising an essential oil (or component thereof) where zinc salts are added to inhibit irritation associated with essential oils. Examples of such patent applications include United States Patent Application Publication No. 20040102429 by Modak et al., published May 27, 2004, and United States Patent Application Publication No. 20050238602 by Modak et al., published Oct. 27, 2005.

U.S. Pat. No. 6,858,317 by Aamodt et al., issued Feb. 22, 2005, relates to methods for protecting wood from mold and sapstaining fungi which employ a non-toxic mold inhibitor which may be a plant extract such as an essential oil.

U.S. Pat. No. 5,100,652 by Kross et al., issued Mar. 31, 1992, relates to low concentration chlorous-acid-generating oral hygiene compositions which may comprise an essential oil as a flavoring agent.

U.S. Pat. No. 5,310,546 by Douglas, issued May 10, 1994, relates to a mouth rinse preparation comprising hydrogen peroxide, zinc chloride, sodium citrate, sodium lauryl sulfate, citric acid and ethanol and optionally an essential oil which is a denaturing agent.

BiON offers several skin care products comprising citric acid, botanicals, and other agents for topical use (San Diego, Calif., US).

Johnson et al. (U.S. Pat. No. 6,319,958 and US20020165130) relates to the use of sesquiterpenoids to promote uptake of exogenous antimicrobial compounds. Similarly, a related article discloses the use of sesquiterpenoids, such as nerolidol, farnesol, bisabolol and apritone, in enhancing bacterial permeability and susceptibility to exogenous antimicrobial compounds, suggesting that sesquiterpenoids have a non-specific and general effect (Brehm-Stecher et al. 2003, Antimicrobial Agents and Chemotherapy, 47(10):3357-3360). In particular, Brehm-Stecher et al. report that nerolidol, farnesol, bisabolol and apritone enhanced the susceptibility of *S. aureus* to the antibiotics erythromycin, gentamicin, vancomycin, ciprofloxacin, clindamycin, and tetracycline.

U.S. Pat. No. 4,867,898 by Spaulding et al., issued Sep. 19, 1989, relates to a liquid hard surface cleaner comprising pine oil and organic, oil-soluble acids at a pH from 0 to 6.

U.S. Pat. No. 6,753,305 by Raso and Caselli, issued Jun. 22, 2004, relates to a hard surface disinfectant comprising up to 20 percent of cinnamon oil or a component thereof, 0.01-5 percent of an organic acid, and optionally an additional essential oil.

International Patent Application Publication No. WO2007077573 by Mukhopadhyay, published Jul. 12, 2007, relates to antimicrobial compositions comprising an antimicrobial agent, such as triclosan, and a functionalized hydrocarbon, where the functionalized hydrocarbon can be an essential oil, and/or a solvent.

There is a continuing desire for an antimicrobial composition that is non-irritating, safe, and effective for repeated use in various professional and non-professional settings.

SUMMARY OF THE INVENTION

The present invention relates to a skin or surface disinfectant composition with broad spectrum antimicrobial activity comprising one or more essential oil (and/or one or more component—i.e., an "Individual Constituent" or "IC"—thereof) and one or more fruit acid. It is based, at least in part, on the discovery that a combination of an essential oil or component thereof together with a fruit acid can confer superior antimicrobial properties on personal care, veterinary, as well as household products. In preferred, non-limiting embodiments, the compositions of the invention further comprise up to about 20 percent alcohol, which facilitates the solubilization of the essential oil(s)/IC(s) and fruit acid. Certain embodiments are also based, at least in part, on the discovery that further addition of an alkanediol, particularly a bifunctional fatty alcohol, enhances antimicrobial activity still more.

In various non-limiting embodiments, the present invention may be utilized in personal care products such as soaps, scrubs, cosmetics, creams and lotions and veterinary products such as pet shampoos and pet cleansing wipes. In other non-limiting embodiments, the present invention may be utilized in household products such as general purpose cleaning fluids, spray cleaners, laundry detergents, food washes, etc.

The compositions of the invention may be used as non-toxic alternatives to conventional disinfectants or may be added to other antimicrobial agents to enhance their activity. The invention provides effective alternatives to harsher products which may be particularly useful in personal care and household products and where children and/or pet exposure may be a concern.

DETAILED DESCRIPTION OF THE INVENTION

For clarity of description, and not by way of limitation, the detailed description of the invention is divided into the following subsections:
(1) essential oils;
(2) fruit acids;
(3) alkanediols;
(4) combinations of essential oils/ICs and fruit acids;
(5) compositions comprising alkanediols;
(6) personal care products;
(7) veterinary products; and
(8) household/industrial products.

4.1 Essential Oils

Essential oils ("EOs"), as defined herein, are volatile oils obtained from plant or animal sources, or their synthetic equivalents, and are composed of complex mixtures of several constituents as monoterpenes and sesquiterpene hydrocarbons, monoterpene and sesquiterpene alcohols, esters, ethers, aldehydes, ketones, oxides and the like. Examples of EOs include, but are not limited to, cinnamon oil, basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginkgo oil, eucalyptus oil, lemon oil, orange oil, and sweet orange oil. In preferred non-limiting embodiments of the invention, the EO is selected from one or more EO from the group consisting of cinnamon oil (bark or leaf), lemongrass oil, citronella oil, basil oil, and orange oil.

Individual constituents ("ICs") of essential oils may be isolated from the oil (natural) or entirely or partially synthetic, and include, but are not limited to, 1-citronellol, a-amylcinnamaldehyde, lyral, geraniol, farnesol, hydroxycitronellal, isoeugenol, eugenol, eucalyptol, linalool, citral, thymol, limonene and menthol. Further examples of ICs include sesquiterpenoid compounds, which may be the active compounds in the essential oils. Sesquiterpenoid compounds, containing 15 carbons, are formed biosynthetically from three 5-carbon isoprene units. Sesquiterpenoid compounds include, but are not limited to, farnesol, nerolidol, bisabolol, apritone, chamazulene, santalol, zingiberol, carotol, and caryophyllen. Mixtures of one or more EO, one or more IC, and one or more EO as well as one or more IC, are encompassed by the present invention. In specific non-limiting embodiments of the invention, an IC is selected from the (non-limiting) group consisting of camphor, alpha-pinene, constituents of cinnamon leaf oil such as cinnamaldehyde, cinnamylacetic ester, cinnamic acid, ethyl cinnamate, methyl chavicol, linalool, beta-caryophyllene, and eugenol; constituents of lemongrass oil such as d-limonene, geranyl acetate, nerol, geraniol, citral, and/or myrcene; constituents of citronella oil such as geraniol, citronellol, citronellal, geranyl acetate, limonene, methyl isoueugenol, and/or elemol; components of basil oil such as camphor, limonene, and/or β-selinene; and constituents of orange oil such as a-pinene, sabinene, myrcene, limonene, linalool, citronellal, neral and/or geranial.

An EO or IC for use in the invention may be obtained from its natural source or may be chemically synthesized.

4.2 Fruit Acids

Fruit acids which may be used according to the invention include but are not limited to citric acid, glycolic acid, lactic acid, malic acid, tartaric acid and acetic acid. In preferred non-limiting embodiments of the invention, the fruit acid is citric acid.

A fruit acid for use in the invention may be obtained from its natural source or may be chemically synthesized.

4.3 Alkanediols

In non-limiting embodiments, bifunctional alcohols which may be used according to the present invention are alkanediols. Suitable alkanediols include, but are not limited to, dodecanediol, decanediol, nonanediol, octanediol, heptanediol, hexanediol and pentanediol.

In particular non-limiting embodiments, the alkanediols have a carbon backbone of between 9 and 25 carbon atoms, including but not limited to 1,9 Nonanediol, 1,2-Decanediol, 1,10-Decanediol, 1,11-Undecanediol, 1,2-Dodecanediol, 1,12 Dodecanediol, Cyclododecanediol, 1,13-Tridecanediol, 1,2-Tetradecanediol, 1,14-Tetradecanediol, 1,15-Pentadecanediol, 1,16-Hexadecanediol, 1,17-Heptadecanediol, 1,18-Octadecanediol, 1,19-Nonadecanediol, 1,20-Eicosanediol, 1,21-Heneicosanediol, 1,22-Docosanediol, 1,23-Tricosanediol, 1,24-Tetracosanediol, 1,25-Pentacosanediol. The preferred alkanediols are 1,2-Decanediol, 1,10-Decanediol, 1,2-Dodecanediol, 1,12-Dodecanediol, Cyclododecanediol, 1,13-Tridecanediol, 1,2-Tetradecanediol, 1,14-Tetradecanediol and the most preferred alkanediols are 1,2-Decanediol, 1,2-Dodecanediol and 1,2-Tetradecanediol.

4.4 Combinations of Essential Oils/ICs and Fruit Acids

The present invention provides for compositions comprising a combination of one or more essential oil (and/or one or more IC thereof) and one or more fruit acid. Preferably, this combination produces a synergistic anti-microbial effect against at least one microbe selected from the group consisting of *Escherichia coli, Pseudomonas aeruginosa, Staphylococcus aureus*, methicillin-resistant *S. aureus*, and *Candida albicans* ("synergistic" means that the antimicrobial effect of the combination is greater than the sum of the antimicrobial effects of the individual components).

In particular, non-limiting embodiments of the invention, the compositions comprise between about 0.1 and 1.0 percent (weight/weight) ("w/w") of one or more essential oils, one or more ICs, or a combination thereof. Where a combination is used, the total of essential oil(s) and/or IC(s) is between about 0.1 and 1.0 percent (weight/weight) and between about 0.125 and 2.0 percent (weight/weight) of one or more fruit acid (where more than one fruit acid is used, the total amount of fruit acids present is between about 0.125 and 2.0 percent (weight/weight). "About" as used in this document means plus or minus 20 percent of the recited value, so that, for example, "between about 0.125 and 1.0 percent" means a range between 0.125±0.025 and 1.0±0.2.

In particular, non-limiting embodiments, the present invention provides for concentrates of essential oil/IC/fruit acid combinations which are concentrated and may be diluted to provide a composition for personal, household, or industrial use. In such concentrates, the ratio of fruit acid to essential oil(s)/IC(s) (weight/weight) is between about 1 and 16, for example, but not by way of limitation, fruit acid(s): EO(s)/IC(s) of between about 1:1 to 10:1, inclusive (weight/weight).

The present invention further provides for methods of providing an antimicrobial effect to a surface comprising applying, to the surface, an effective amount of a composition as described herein. An antimicrobial effect means killing and/or inhibiting the growth/proliferation of a microbe. In particular non-limiting embodiments of the invention, the microbe is selected from the group consisting of from the group consisting of *Escherichia coli, Pseudomonas aeruginosa, Staphylococcus aureus*, methicillin-resistant *S. aureus*, and *Candida albicans*. In specific non-limiting embodiments, the composition is exposed to the surface for at least 20 seconds, at least 30 seconds, or at least 60 seconds, or at least 5 minutes or at least 10 minutes. In various non-limiting embodiments, the surface may be the a skin or mucosal surface, a household surface (e.g., a surface of a countertop, table sink, toilet, wall, floor, appliance, window, shower surface, rug, upholstery, fabric, etc.) or an industrial surface (e.g., a surface of a countertop, table sink, toilet, wall, floor, appliance, window, shower surface, rug, upholstery, fabric, etc.).

In a first set of specific, non-limiting embodiments, the present invention provides for a composition comprising a component selected from the group consisting of cinnamon oil, cinnamaldehyde, eugenol, cinnamylacetic ester, and cinnamic acid, at a concentration of between about 0.1 and 1.2 percent (weight/weight) or between about 0.2 and 0.6 percent (weight/weight), as well as citric acid at a concentration of between about 0.5 and 1.5 percent (weight/weight), optionally further comprising triclosan at a concentration of between about 0.05 and 3 percent (weight/weight) or between about 0.05 and 0.1 percent (weight/weight) (this range, and all ranges herein, inclusive). In certain embodiments, the EO/IC is not cinnamon oil or pine oil or an IC thereof.

In a second set of non-limiting embodiments, the present invention provides for compositions comprising a EO/IC mixture comprising two or more EO or IC from the group consisting of cinnamon oil or an IC thereof, lemongrass oil and/or an IC thereof, orange oil and/or an IC thereof, basil oil and/or an IC thereof, and citronella oil and/or an IC thereof, at a total EO/IC concentration of between about 0.1 and 1 percent (weight/weight); together with one or more fruit acid (preferably citric acid), at a total fruit acid concentration of between about 0.125 and 2 percent (weight/weight); and an alcohol (preferably ethanol at a concentration of between about 5-20 percent (weight/weight), optionally further comprising triclosan at a concentration of between about 0.05 and 3 percent (weight/weight) or between about 0.05 and 0.1 percent (weight/weight), where the ratio of EO/IC to fruit acid is between about 1:1 to about 1:10. In certain embodiments, the EO/IC is not cinnamon oil or pine oil or an IC thereof.

In a third set of non-limiting embodiments, the present invention provides for compositions comprising a EO/IC mixture comprising lemongrass oil and/or an IC thereof, orange oil and/or an IC thereof, and optionally one or more additional EO and/or IC, at a total EO/IC concentration of between about 0.1 and 1 percent (weight/weight); together with one or more fruit acid (preferably citric acid), at a total fruit acid concentration of between about 0.125 and 2 percent; and an alcohol (preferably ethanol) at a concentration of between about 5-20 percent (weight/weight), optionally further comprising triclosan at a concentration of between about 0.05 and 1 percent (weight/weight) or between about 0.05 and 0.3 percent (weight/weight), where the ratio of EO/IC to fruit acid is between about 1:1 to about 1:10.

4.5 Compositions Comprising Alkanediols

In non-limiting embodiments, the present invention provides for compositions comprising an essential oil, a fruit acid, an alcohol which is not an alkanediol, and an alkanediol. In particular, non-limiting embodiments, the carbon backbone of the alkanediol has between 9 and 25 carbon atoms.

In particular non-limiting embodiments, the present invention provides for compositions comprising (i) between about 0.2 and 0.7 percent (weight/weight) of one or more essential oil as set forth above and preferably selected from the group consisting of lemongrass, cinnamon oil, citronella oil, basil oil, orange oil and combinations thereof; (ii) a non-alkanediol alcohol solvent at a concentration between about 0.5 and 20 percent (weight/weight); (iii) an amount of alkanediol which increases the antimicrobial effect, for example at a concentration between about 0.3 and 1.0 percent (weight/weight), and (iv) one or more fruit acid at a total concentration between about 0.125 and 2.0 percent (weight/weight).

The preferred essential oils are the ones that show significant enhancement of antimicrobial activity in combination with citric acid. These oils include one or more selected from lemongrass oil, cinnamon oil, basil oil and citronella oil, preferably at a total concentration of between about 0.2 and 0.7 percent (weight/weight), with the optional further addition of orange oil to reduce the pungent odor of the other essential oils and to provide a fragrance which is mild and pleasant. Fruit acids which may be used in such compositions include citric acid or lactic acid (preferably citric acid) at a concentration between about 0.5 and 1.0 percent (weight/weight).

Preferred but non-limiting examples of non-alkanediol alcohols for solubilization of both essential oils and citric acid are aliphatic alcohols having carbon atoms about 1 to 8 such as methanol, ethanol, n-propanol, isopropyl alcohol, 2-methyl-2 propanol, hexanol, or combinations thereof, at a concentration of between about 5 and 20 percent (weight/weight). Aromatic alcohols, for example, but not by way of limitation, phenoxyethanol, benzyl alcohol, 1-phenoxy-2propanol, and/or phenethyl alcohol, for example at a concentration of between about 0.5 and 5 percent (weight/weight), may also optionally be used in combination with aliphatic alcohols. A further solvent which optionally may be comprised in a composition of the invention is isopropyl myristate. Most preferred aliphatic alcohols include ethanol, denatured alcohol (SDA 40B and SDA3C) and isopropanol. Most preferred aromatic alcohols include phenoxyethanol and phenethanol.

Compositions comprising lemongrass or cinnamon oils (0.2-0.5 percent) and orange oil (0.1-0.2 percent) exhibit a pleasant and mild fragrance. Furthermore these oils even at these lower concentrations have been observed to provide superior antibacterial activity (more than 3 log reduction when challenged with $10^8$ colony forming unit of a gram-positive pathogen (*S. aureus*) in combination with a secondary alcohol (0.3-1.0%) and alcohol (5-20%).

In specific, non-limiting embodiments, the present invention provides for a skin or surface disinfectant composition comprising the essential oil lemongrass (0.3-0.5 percent (weight/weight)), orange oil (0.1-0.2 percent (weight/weight)), citric acid (0.5-2.0 percent (weight/weight)), SDA 40B alcohol (5-20 percent (weight/weight)) and 1,2 decanediol (0.3-1.0 percent (weight/weight)).

Preferably the pH of personal care products is in the range of about 3.5-5.0, and more preferably in the range of about 4-4.7.

In addition to the above ingredients, a composition of the invention may optionally further comprise an emollient to further reduce irritation, such as, but not limited to, a fatty alcohol, behentrimonium methosulfate-cetyl alcohol (Incroquat TMS), or a polyol such as glycerol, propylene glycol, diglycerol, ethylene glycol, diethylene glycol, triethylene glycol, dipropylene glycol, tripropylene glycol, hexylene glycol, butylene glycol, etc.

Essential oils are volatile and therefore it is desirable that the antimicrobial composition containing essential oils is incorporated in a suitable base in which it is stable at higher temperature and over a long period of time. Accordingly, a composition of the invention may optionally comprise a hydrophilic or hydrophobic gel-forming polymer, a fatty acids, a plant oils etc. Suitable hydrophilic gel polymers include, but are not limited to, hydroxypropylmethyl cellulose, cationic hydroxyethyl cellulose (UCARE polymers), ethyl cellulose, hydroxypropyl cellulose, hydroxymethyl cellulose, carboxy methyl cellulose, polyethylene oxide (POLYOX resins), and chitosan pyrrolidone carboxylate (KYTAMER PC), silica gel, carbomerpolymers etc. Suitable hydrophobic gel polymers include, but are not limited to, silicone polymers, for example polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C and Q2-5220 Silicone Fluid), silicone glycol (BASF 1066 DCG polyol), KSG series silicone gels (Shin-etsu), and combinations thereof. Suitable plant oils include, but are not limited to, olive oil, almond oil, avocado oil, basil oil, primrose oil, peanut oil, safflower oil, sesame oil, soybean oil, and wheat germ oil.

4.6 Personal Care Products

In non-limiting embodiments, the present invention provides for personal care product compositions comprising a combination of one or more essential oil and/or IC together with one or more fruit acid, as set forth in section 4.4 or 4.5, above. In preferred, non-limiting embodiments, the amounts of the active agents are such that regular exposure of skin to the personal care product does not produce skin irritation in a normal subject.

Non-limiting examples of personal care products which may utilize the invention include bar soap, liquid soap (e.g. hand soap), hand sanitizer, cleansing wipes, body wash, acne treatment products, shampoo, conditioner, cosmetics (including but not limited to liquid or powder foundation, liquid or solid eyeliner, mascara, cream eye shadow, tinted powder, "pancake" type powder to be used dry or moistened, etc.), deodorant, body lotion, hand cream, topical cream, aftershave lotion, skin toner, mouth wash, toothpaste, sunscreen lotion, and baby products such as, but not limited to, cleansing wipes, baby shampoo, baby soap, and diaper cream. The present invention may also be applied to wound care items, such as, but not limited to, wound coverings, bandages, tape, and Steri-Strips, and medical articles such as medical gowns, caps, face masks, shoe-covers, surgical drops, etc.

Personal care compositions according to the invention, in addition to one or more essential oil and/or IC together with one or more fruit acid, may further comprise one or (preferably) more than one component selected from the group consisting of emollients, stabilizing agents, thickening agents, humectants, antimicrobial agents, neutralizing agents, surfactants, water, silicone polymers, alcohols, and hydrogels, as well as additional components as may be known in the art. Non-limiting examples of such components are set forth below.

In various non-limiting embodiments of the invention, a personal care product comprising a combination of one or more essential oil and/or IC together with one or more fruit acid may further comprise an emollient, for example PEG 20 almond glycerides, Probutyl DB-10, Glucam P-20, Glucam E-10, Glucam P-10, Glucam E-20, Glucam P-20 distearate, Glycerine, propylene glycol, octoxyglycerine, cetyl acetate, acetylated lanolin alcohol (e.g., Acetulan), cetyl ether (e.g., PPG-10), myristyl ether (e.g., PPG-3), hydroxylated milk glycerides (e.g., Cremeral HMG), polyquatemium compounds (e.g., UCARE compounds), copolymers of dimethyl dialyl ammonium chloride and acrylic acid (e.g., Merquat), dipropylene glycol methyl ethers (e.g., DOWANOL DPM, Dow Corning), polypropylene glycol ethers (e.g., UCON 50-HB-600, Union Carbide) and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

In various non-limiting embodiments of the invention, a personal care product comprising a combination of one or more essential oil and/or IC together with one or more fruit acid may further comprise a stabilizing agent consisting of antioxidants, including but not limited to vitamin C (ascorbic acid) and vitamin E (tocopherol), and surfactants, including but not limited to Incromine or silicone-based surfactants (MASIL SF-19, BASF).

In various non-limiting embodiments of the invention, a personal care product comprising a combination of one or more essential oil and/or IC together with one or more fruit acid may further comprise a thickening agent such as stearyl alcohol, cationic hydroxy ethyl cellulose (UCARE JR-30), hydroxy propyl methyl cellulose, hydroxy propyl cellulose (Klucel), chitosan pyrrolidone carboxylate (KYTAMER PC), behenyl alcohol, zinc stearate, emulsifying waxes, including but not limited to Incroquat and Polawax, an addition polymer of acrylic acid, a resin such as Carbopol®

ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-SM, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/Glycerine/glycidyl decanoate copolymer, ophthalmic/trimellitic/glycols copolymer, polybutene, polybutylene terephthalate, polydi pentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearalkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

In various non-limiting embodiments of the invention, a personal care product comprising a combination of one or more essential oil and/or IC together with one or more fruit acid may further comprise a humectant, such as, for example, Glycerine, 1-2-propylene glycol, dipropylene glycol, polyethylene glycol, 1,3-butylene glycol, or 1,2,6-hexanetriol.

In certain non-limiting embodiments of the invention, essentially the entire antimicrobial effect of the inventive composition is achieved by an antimicrobial composition consisting of one or more essential oil and/or one or more IC, together with a fruit acid and optionally an alcohol. In alternative embodiments of the invention, one or more additional antimicrobial agent may be comprised, for example, in the amount of between about 0.05 and 2.0 percent (weight/weight), where such antimicrobial agent may be selected from the group consisting of iodophors, iodine, benzoic acid, dihydroacetic acid, propionic acid, sorbic acid, methyl paraben, ethyl paraben, propyl paraben, butyl paraben, cetrimide, benzalkonium chloride, dequalinium chloride, chlorhexidine, chloroeresol, chloroxylenol, benzyl alcohol, bronopol, chlorbutanol, phenoxyethanol, phenylethyl alcohol, 2,4-dichlorobenzyl alcohol, thimerosal, clindamycin, erythromycin, benzoyl peroxide, mupirocin, bacitracin, polymyxin B, neomycin, triclosan, parachlorometaxylene, foscamet, miconazole, fluconazole, itriconazole, ketoconazole, silver sulfadiazine, octoxyglycerine, biguanides such as, but not limited to, chlorhexidine free base, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-a-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, and parahexamethylenebiguanide ("PHMB").

In various non-limiting embodiments of the invention, a personal care product comprising a combination of one or more essential oil and/or IC together with one or more fruit acid may further comprise a neutralizing agent to neutralize carboxyl groups present in one or more other component, such as carboxyl groups in a thickening agent. Suitable neutralizing agents include diisopropylamine and triethanolamine.

In various non-limiting embodiments of the invention, a personal care product comprising a combination of one or more essential oil and/or IC together with one or more fruit acid may further comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ" ® nonionic surfactants available from ICI Americas, Inc. (Wilmington, Del.)), cocamidopropyl betaine, alkyl phenols, fatty acid esters of sorbitol, sorbitan, or POLYOXyethylene sorbitan. Suitable anionic surfactants include ammonium lauryl sulfate and lauryl ether sulfosuccinate. A preferred surfactant is lauroyl ethylenediamine triacetic acid sodium salt at a concentration between about 0.5% and 2.0%. In particular non-limiting embodiments of the invention, concentrations of surfactant are between about 0.05% and 2%.

In various non-limiting embodiments of the invention, a personal care product may comprise water.

In various non-limiting embodiments of the invention, a personal care product comprising a combination of one or more essential oil and/or IC together with one or more fruit acid may further comprise a hydrogel comprising, for example, a compound such as hydroxypropylmethyl cellulose, cationic hydroxyethyl cellulose (UCARE polymers), ethyl cellulose, hydroxypropyl cellulose, hydroxymethyl cellulose, carboxy methyl cellulose, polyethylene oxide (POLYOX resins), and chitosan pyrrolidone carboxylate (KYTAMER PC).

In various non-limiting embodiments of the invention, a personal care product comprising a combination of one or more essential oil and/or IC together with one or more fruit acid may further comprise an alcohol or a mixture of alcohols, for example, ethanol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol.

In various non-limiting embodiments of the invention, a personal care product comprising a combination of one or more essential oil and/or IC together with one or more fruit acid may further comprise a silicone polymer, for example one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), and silicone glycol (BASF 1066 DCG polyol). In particular, non-limiting embodiments, the amount of silicone polymer is between about 0.1 and 1.0 percent (volume/volume).

In various non-limiting embodiments of the invention, a personal care product comprising a combination of one or more essential oil and/or IC together with one or more fruit acid may further comprise an emollient solvent such as a glycidyl ether having an alkyl chain up to and including 18 carbon molecules and ethoxylates and propoxylates thereof, a glyceryl ether having an alkyl chain up to and including 18 carbon molecules and ethoxylates and propoxylates thereof, a mono- or diglyceryl ether having an alkyl chain up to and including 18 carbon molecules and ethoxylates and propoxylates thereof, ethoxylate and propoxylate ethers, ethoxy diglycol esters, ethyl hexyl alcohol propoxylate, and propylene glycol esther ethoxylates and propoxylates, and Arlamol (Altas).

In various non-limiting embodiments of the invention, a personal care product comprising a combination of one or more essential oil and/or IC together with one or more fruit acid may further comprise additives such as dyes, fragrances, pH adjusters, including basic pH adjusters such as ammonia, mono-, di- and tri-alkyl amines, mono-, di- and tri-alkanolamines, alkali metal and alkaline eaiih metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as Germall Plus and DMDM hydantoin, and sunscreens such as aminobenzoic acid, arobenzone, cinoxate, dioxybenzone, homosalate, menthyl anthranilate, octocrylene, octyl methoxycinnamate, octyl salicylate, oxybenzoate, padimate 0, phenylbenzimidazole, sulfonic acid, sulisobenzone, titanium dioxide, trolamine salicylate and zinc oxide.

In one set of non-limiting embodiments, the present invention provides for personal care compositions comprising one or more EO/IC, preferably where the EO(s)/IC(s) are selected from the group consisting of lemongrass oil and/or an IC thereof, orange oil and/or an IC thereof, cinnamon leaf oil and/or an IC thereof, basil oil and/or an IC thereof, eugenol, cinnamaldehyde, cinnamylacetic ester, and cinnamic acid, at a total concentration of between about 0.1 and 1 percent (weight/weight); a fruit acid, preferably citric acid, at a concentration of between about 0.125 and 1 percent (weight/weight); an alcohol, preferably ethanol, at a concentration of between about 5 and 20 percent (weight/weight); and optionally triclosan at a concentration of between about 0.05 and 1 percent (weight/weight), where the ratio of EO(s)/IC(s) to the fruit acid(s) is between about 1:1 to 1:10 and the pH is between about 3 and about 7, preferably between 5 and 6.

In another set of non-limiting embodiments, the present invention provides for personal care compositions comprising lemongrass oil or an IC thereof and orange oil or an IC thereof at a total concentration of between about 0.2 and 0.7 percent (weight/weight); a fruit acid, preferably citric acid, at a concentration of between about 0.25 and 1 percent (weight/weight); an alcohol, preferably ethanol, at a concentration of between about 5 and 20 percent (weight/weight); and optionally triclosan at a concentration of between about 0.05 and 1 percent (weight/weight), where the ratio of EO(s)/IC(s) to fruit acid(s) is between about 1:1 to 1:5 and the pH is between about 3 and about 7, preferably between 5 and 6.

In one specific, non-limiting embodiment, the present invention provides for a liquid soap product called "CN1-A" having the following composition:

| Ingredients | (weight/weight) |
| --- | --- |
| Deionized water | 59.15% |
| POLYOX N-60K | 0.2% |
| Pluronic F87 Prill | 2.0% |
| UCARE JR-30 | 0.4% |
| DL-Panthenol 50 W | 1.0% |

| Ingredients | (weight/weight) |
| --- | --- |
| Incromine oxide L | 3.0% |
| Crosultane C-50 | 3.0% |
| Montalene C 40 | 3.0% |
| 2-Phenoxy-ethanol | 1.0% |
| Zinc gluconate | 0.1% |
| Glycerine | 2.0% |
| SDA 40B alcohol | 15.5% |
| Cinnamon leaf oil | 0.5% |
| Citric acid | 1.0% |
| Orange oil | 0.2% |
| Distilled water | 7.95% |

In another specific, non-limiting embodiment, the present invention provides for a liquid soap product called "CN1-B" having the following composition:

| Ingredients | (weight/weight) |
| --- | --- |
| Deionized water | 63.2% |
| METHOCEL 40-101 | 0.1% |
| Pluronic F87 Prill | 0.1% |
| UCARE JR-30 | 0.1% |
| DL-Panthenol 50 W | 1.0% |
| Incromine oxide L | 3.0% |
| Crosultane C-50 | 3.0% |
| Montalene C 40 | 1.5% |
| 2-Phenoxy-ethanol | 1.0% |
| Glycerine | 2.0% |
| SDA 40B alcohol | 15.5% |
| Cinnamon leaf oil | 0.5% |
| Citric acid | 1.0% |
| Orange oil | 0.2% |
| Distilled water | 7.8% |

In another specific, non-limiting embodiment, the present invention provides for a liquid soap product called "CN1-C" having the following composition:

| Ingredients | (weight/weight) |
| --- | --- |
| Deionized water | 63.2% |
| METHOCEL 40-101 | 0.1% |
| Pluronic F87 Prill | 0.1% |
| UCARE JR-30 | 0.1% |
| DL-Panthenol 50 W | 1.0% |
| Incromine oxide L | 3.0% |
| Crosultane C-50 | 3.0% |
| Montalene C 40 | 1.5% |
| 2-Phenyl-ethanol | 1.0% |
| Glycerine | 2.0% |
| SDA 40B alcohol | 15.5% |
| Cinnamon leaf oil | 0.5% |
| Citric acid | 1.0% |
| Orange oil | 0.2% |
| Distilled water | 7.8% |

In a subset of non-limiting embodiments, the present invention provides for a soap comprising one or more essential oil, 1% citric acid, and a soap base comprising a surfactant, an emollient, and a thickener, and having a pH between about 3 and 5. Specific non-limiting examples of such soaps follow.

Soap Containing Lemongrass oil and Citric acid (LG-Cit 4)
(4 represents total oil 0.4%)

| Ingredients | Percentage (w/w) |
| --- | --- |
| Deionized water | 63.5 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Lemongrass oil | 0.4 |

Soap Containing Lemongrass oil and Citric acid (LG-Cit 6)
(6 represents total oil 0.6%)

| Ingredients | Percentage (w/w) |
| --- | --- |
| Deionized Water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Lemongrass oil | 0.6 |

Soap Containing Lemongrass oil, Orange oil (O) and Citric acid (LGO-Cit 6)
(6 represents total oil 0.6%)

| Ingredients | Percentage (w/w) |
| --- | --- |
| Deionized Water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Lemongrass oil | 0.4 |
| Citric acid | 1.0 |
| Orange oil | 0.2 |

Soap Containing Lemongrass oil, Orange oil and Citric acid (LGO-Cit 7)
(7 represents total oil 0.7%)

| Ingredients | Percentage (w/w) |
| --- | --- |
| Deionized water | 63.2 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |

-continued

| Ingredients | Percentage (w/w) |
| --- | --- |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Lemongrass oil | 0.5 |
| Citric acid | 1.0 |
| Orange oil | 0.2 |

Soap Containing Cinnamon oil, Orange oil and Citric acid (CO-Cit 6)

(6 represents total oil 0.6%)

| Ingredients | Percentage (w/w) |
| --- | --- |
| Deionized water | 63.3 |
| METHOCEL 40-101 | 0.1 |
| Pluronic F87 Prill | 0.1 |
| UCARE JR-30 | 0.1 |
| DL Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Cinnamon oil | 0.4 |
| Citric acid | 1.0 |
| Orange oil | 0.2 |

Soap Containing Cinnamon oil, Orange oil and Citric acid (CO-Cit 7)

(7 represents total oil 0.7%)

| Ingredients | Percentage (w/w) |
| --- | --- |
| Deionized water | 63.2 |
| METHOCEL 40-101 | 0.1 |
| Pluronic F87 Prill | 0.1 |
| UCARE JR-30 | 0.1 |
| DL-Panthenol 50 W | 1.0 |
| Incromine oxide L | 3.0 |
| Crosultane C-50 | 3.0 |
| Montalene C 40 | 1.5 |
| 2-Phenoxy-ethanol | 1.0 |
| Glycerine | 2.0 |
| SDA 40B | 15.5 |
| Cinnamon oil | 0.5 |
| Citric acid | 1.0 |
| Orange oil | 0.2 |

Soap Containing Orange oil and Citric acid (O-Cit 2)

(2 represents total oil 0.2%)

| Ingredients | Percentage (w/w) |
| --- | --- |
| Deionized water | 63.7 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |

-continued

| Ingredients | Percentage (w/w) |
| --- | --- |
| Glycerine | 2.0 |
| SDA 40B | 15.5 |
| Orange oil | 0.2 |
| Citric acid | 1.0 |

Soap Containing Basil oil (B), Orange oil and Citric acid (BO-Cit 6)

(6 represents total oil 0.6%)

| Ingredients | Percentage (w/w) |
| --- | --- |
| Deionized water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Basil oil | 0.4 |
| Citric acid | 1.0 |
| Orange oil | 0.2 |

Soap Containing Citronella oil (CR), Orange oil and Citric acid (CRO-Cit 6)

(6 represents total oil 0.6%)

| Ingredients | Percentage (w/w) |
| --- | --- |
| Deionized water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Citronella oil | 0.4 |
| Citric acid | 1.0 |
| Orange oil | 0.2 |

In further specific, non-limiting embodiments, the present invention provides for the following combinations of agents in a soap base (percentages w/w):
  0.15% TC+0.4% lemongrass oil+0.2% orange oil+1% citric acid; or
  0.4% lemongrass oil+0.2% orange oil+1% citric acid; or
  0.15% TC+0.4% cinnamon oil+0.2% orange oil+1% citric acid; or
  0.4% cinnamon oil+0.2% orange oil+1% citric acid.

In still further specific, non-limiting embodiments, the present invention provides for the following combinations of agents in a soap base (percentages w/w):
  Cinnamon oil 0.5%+Orange oil 0.2%+Citric acid 1.0%+alcohol (e.g., denatured ethyl alcohol, such as SDA 40 B) 5.5%+TC 0.14% (or TC 0.15%); or
  Lemongrass oil 0.5%+Orange oil 0.2%+Citric acid 1.0%+alcohol (e.g., denatured ethyl alcohol, such as SDA 40B) 5.5%+TC 0.14% (or TC 0.15%); or
  Lemongrass oil 0.5%+Citric acid 1.0%+alcohol (e.g. denatured ethyl alcohol such as SDA 40 B) 5.5%+TC 0.14% (or TC 0.15%).

In specific non-limiting embodiments, the present invention provides for compositions comprising 0.2-0.3 percent (weight/weight) of essential oils such as lemongrass or cinnamon and 0.1-0.2 percent (weight/weight) orange oil when used in combination with 1% citric acid and alkanediols such as 1,2 decanediol, 1,2 dodecanediol and 1,12 dodecanediol, as set forth above. In a specific, non-limiting embodiment, the present invention provides for a soap formulation comprising 0.3% of lemongrass oil or cinnamon oil in combination with 0.1% orange oil, and 1% citric acid with and without alkanediols, where the pH preferably is between 4.5 and 4.6.

Soap containing Lemongrass oil, Orange oil and Citric acid (LG-0-Cit 5)
(5 represents total oil 0.5%)

| Ingredients | Percentage (w/w) |
| --- | --- |
| Deionized water | 64.8 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.2 | pH 4.55

Soap Containing Lemongrass oil, Orange oil and Citric acid (LG-0-Cit 4)
(4 represents total oil 0.4%)

| Ingredients | Percentage (w/w) |
| --- | --- |
| Deionized water | 64.9 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.1 | pH 4.64

Soap Containing LG-0-Cit 5 and 0.3% 1,2 Decanediol

| Ingredients | Percentage (w/w) |
| --- | --- |
| Deionized water | 64.5 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.2 |
| 1,2 Decanediol | 0.3 | pH 4.6

Soap Containing LG-0-Cit 4 and 0.3% 1,2 Decanediol

| Ingredients | Percentage (w/w) |
| --- | --- |
| Deionized water | 64.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.1 |
| 1,2 Decanediol | 0.3 | pH 4.6

Soap Containing LG-0-Cit 4 and 0.3% 1,2 Decanediol+ 0.5% Incroquat Behenyl TMS

| Ingredients | Percentage (w/w) |
| --- | --- |
| Deionized water | 64.1 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.1 |
| 1,2 Decanediol | 0.3 |
| Incroquat TMS | 0.5 | pH 4.6

Soap Containing LG-0-Cit 4 and 0.3% 1,2 Dodecanediol

| Ingredients | Percentage (w/w) |
| --- | --- |
| Deionized water | 64.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |

Soap Containing LG-O-Cit 4 and 0.3% 1,12 Dodecanediol

| Ingredients | Percentage (w/w) |
| --- | --- |
| Deionized water | 64.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.1 |
| 1,12 Dodecanediol | 0.3 |

Soap Containing LG-O-Cit 4 and 0.3% 1,2 Tetradecanediol

| Ingredients | Percentage (w/w) |
| --- | --- |
| Deionized water | 64.6 |
| METHOCEL 40-101 | 0.2 |
| Pluronic F87 Prill | 1.0 |
| POLYOX WSR-N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 15.0 |
| Lemongrass oil | 0.3 |
| Citric acid | 1.0 |
| Orange oil | 0.1 |
| 1,2 Tetradecanediol | 0.3 |

Soap Containing LG-O-Cit 4A
(Same as LG-O-Cit 4 but contains 17% SDA 40B alcohol instead of 15%)

| Ingredients | Percentage (w/w) |
| --- | --- |
| Deionized water | 62.9 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |
| Lemongrass oil | 0.3 |
| Citric acid | 1.0 |
| Orange oil | 0.1 | pH 4.64

Soap Containing LG-O-Cit 4A and 0.5% 1,2 Decanediol

| Ingredients | Percentage (w/w) |
| --- | --- |
| Deionized water | 62.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |
| Lemongrass oil | 0.3 |
| Citric acid | 1.0 |
| Orange oil | 0.1 |
| 1,2 Decanediol | 0.5 | pH 4.6

Soap Containing LG-O-Cit 4A and 0.5% 1,2 Dodecanediol

| Ingredients | Percentage (w/w) |
| --- | --- |
| Deionized water | 62.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |
| Lemongrass oil | 0.3 |
| Citric acid | 1.0 |
| Orange oil | 0.1 |
| 1,2 Decanediol | 0.5 | pH 4.6

Soap Containing LG-O-Cit 4A and 0.5% 1,12 Dodecanediol

| Ingredients | Percentage (w/w) |
| --- | --- |
| Deionized water | 62.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |

-continued

| Ingredients | Percentage (w/w) |
|---|---|
| Lemongrass oil | 0.3 |
| Citric acid | 1.0 |
| Orange oil | 0.1 |
| 1,12 Decanediol | 0.5 | pH 4.6

Soap Containing LG-O-Cit 4A and 0.5% 1,2 Tetradecanediol

| Ingredients | Percentage (w/w) |
|---|---|
| Deionized water | 62.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |
| Lemongrass oil | 0.3 |
| Citric acid | 1.0 |
| Orange oil | 0.1 |
| 1,2 Tetradecanediol | 0.5 | pH 4.6

Soap Containing Cn-O-Cit 4A

| Ingredients | Percentage (w/w) |
|---|---|
| Deionized water | 62.9 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |
| Cinnamon oil | 0.3 |
| Citric acid | 1.0 |
| Orange oil | 0.1 | pH 4.64

Soap Containing Cn-O-Cit 4A+0.5% 1,2 Decanediol

| Ingredient | Percentage (w/w) |
|---|---|
| Deionized water | 62.6 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 |
| SDA 40B | 17.0 |
| Cinnamon oil | 0.3 |
| Citric acid | 1.0 |
| Orange oil | 0.1 |
| 1,2 Decanediol | 0.5 | pH 4.64

Soap Base

| Ingredients | Percentage (w/w) |
|---|---|
| Deionized water | 81.3 |
| METHOCEL 40-101 | 0.2 |
| Pluronic F87 Prill | 1.0 |
| POLYOX WSR N-60K | 0.2 |
| UCARE JR-30 | 0.3 |
| DL-Panthenol 50 W | 1.0 |
| Incromine Oxide L | 8.0 |
| Crosultane C-50 | 3.0 |
| Montalene C 40 | 2.0 |
| 2-Phenoxy-Ethanol | 1.0 |
| Glycerine | 2.0 | pH 4.64 (adjusted with 10N hydrochloric acid)

An antibacterial topical lotion comprising LG-O-Cit A+1,2 Decanediol ("LG-O-Cit A-D Lotion"):

| Constituent | % (w/w) |
|---|---|
| Water | 65.9 |
| UCARE JR-30M | 0.25 |
| POLYOX WSR-205 | 0.1 |
| Incroquat Behenyl TMS | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerine | 2.0 |
| Allantoin | 0.2 |
| Dimethicone copolyol (Q2-5220) | 2.5 |
| Citric acid | 1.0 |
| 1,2 Decanediol | 0.5 |
| Tocopheryl acetate | 0.5 |
| Glyceryl stearate (Arlacel 165) | 1.0 |
| Butylene glycol | 3.0 |
| SDA 40B | 15.0 |
| Lemongrass oil | 0.5 |
| Tea tree oil | 0.5 |
| Orange oil | 0.1 |
| 1,2 Decanediol (SymClairol) | 0.5 |

(pH adjusted to 4.5-5.0)

An antibacterial topical lotion comprising LG-O-Cit A+1,2 Decanediol+Triclosan ("LG-O-Cit A-D-T Lotion"):

| Constituent | % (w/w) |
|---|---|
| Water | 65.6 |
| UCARE JR-30 | 0.25 |
| POLYOX WSR-205 | 0.1 |
| Incroquat Behenyl TMS | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerine | 2.0 |
| Allantoin | 0.2 |
| Dimethicone copolyol (Q2-5220) | 2.5 |
| Citric acid | 1.0 |
| 1,2 Decanediol | 0.5 |

| Constituent | % (w/w) |
| --- | --- |
| Tocopheryl acetate | 0.5 |
| Glyceryl stearate (Arlacel 165) | 1.0 |
| Butylene glycol | 3.0 |
| SDA 40B | 15.0 |
| Lemongrass oil | 0.5 |
| Tea tree oil | 0.5 |
| Orange oil | 0.1 |
| 1,2 Decanediol (SymClairol) | 0.5 |
| Triclosan | 0.3 |

(pH adjusted to 4.5-5.0)

An antibacterial-anti inflammatory topical lotion comprising LG-O-CitA+1,2 Decanediol ("LG-O-Cit A-D AB/AIF Lotion"):

| Constituent | % (w/w) |
| --- | --- |
| Water | 65.6 |
| UCARE JR-30 | 0.25 |
| POLYOX WSR-205 | 0.1 |
| Incroquat Behenyl TMS | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerine | 2.0 |
| Allantoin | 0.2 |
| Dimethicone copolyol (Q2-5220) | 2.5 |
| Citric acid | 1.0 |
| 1,2 Decanediol | 0.5 |
| Tocopheryl acetate | 0.5 |
| Glyceryl stearate (Arlacel 165) | 1.0 |
| Butylene glycol | 3.0 |
| SDA 40B | 15.0 |
| Lemongrass oil | 0.5 |
| Tea tree oil | 0.5 |
| Orange oil | 0.1 |
| 1,2 Decanediol (SymClairol) | 0.5 |
| Curcumin | 0.2 |
| Camphor | 0.1 |

(pH adjusted to 4.5-5.0)

Preservative Composition A

| Ingredients | % (w/w) |
| --- | --- |
| Lemongrass oil | 10 |
| Farnesol | 10 |
| Orange oil | 5 |
| Lactic acid | 7 |
| 1,2 Decanediol | 7 |
| SDA 40B alcohol | 61 |

Preservative Composition B

| Ingredients | % (w/w) |
| --- | --- |
| Lemongrass oil | 15 |
| Farnesol | 15 |
| Orange oil | 10 |
| Lactic acid | 10 |
| SDA 40B alcohol | 50 |

Preservative Composition C

| Ingredients | % (w/w) |
| --- | --- |
| Farnesol | 17 |
| Citric acid | 7 |
| 1,2 Decanediol | 7 |
| SDA 40B alcohol | 69 |

Preservative Composition D

| Ingredients | % (w/w) |
| --- | --- |
| Lemongrass oil | 15 |
| Orange oil | 5 |
| Lactic acid | 10 |
| 1,2 Decanediol | 20 |
| 1,2 Octanediol | 20 |
| SDA 40B alcohol | 30 |

Preservative Composition E

| Ingredients | % (w/w) |
| --- | --- |
| Lemongrass oil | 15 |
| Orange oil | 5 |
| Lactic acid | 10 |
| 1,2 Octanediol | 40 |
| SDA 40B alcohol | 30 |

The pH of these solutions are adjusted to 5.0. Of these preservatives, 0.5-5.0% can be used in various formulations.

Antimicrobial Impregnation Solution

| Ingredients | % (w/w) |
| --- | --- |
| Lemongrass oil | 0.3 |
| Orange oil | 0.1 |
| Tea tree oil | 0.5 |
| *Calendula* oil | 0.5 |
| Citric acid | 1.0 |
| Olive oil | 5.0 |
| Propylene glycol | 10 |
| Decanediol | 0.5 |
| SDA 40B alcohol | 51.7 |
| UCARE JR-30 | 0.4 |
| Water | 30 |

Antimicrobial/Anti-Inflammatory Impregnation Solution

| Ingredients | % (w/w) |
| --- | --- |
| Lemongrass oil | 0.3 |
| Orange oil | 0.1 |
| Tea tree oil | 0.5 |
| *Calendula* oil | 0.5 |
| Citric acid | 1.0 |
| Olive oil | 5.0 |
| Propylene glycol | 10 |
| Decanediol | 0.5 |
| SDA 40B alcohol | 51.0 |
| UCARE JR-30 | 0.4 |

| Ingredients | % (w/w) |
|---|---|
| Curcumin | 0.3 |
| Water | 29.7 |

4.7 Veterinary Products

In a subset of non-limiting embodiments, the present invention provides for veterinary products comprising a combination of one or more essential oil and/or IC together with one or more fruit acid, as set forth in section 4.4 or 4.5, above. The term "veterinary", as used here, means "pet care", and includes home use as well as use in a veterinary office or other pet care establishment.

Non-limiting examples of veterinary care products which may utilize the invention include pet shampoo, pet cleansing wipes including body wipes, ear wipes, and eye wipes, ear cleaning liquid, cage cleaner, surface cleaner for housebreaking accidents, topical creams, teat dip therapeutic for mastitis and liquid to be applied to pet's skin (as in a "body splash").

Veterinary care compositions according to the invention, in addition to one or more essential oil and/or IC together with one or more fruit acid, may further comprise one or (preferably) more than one component selected from the group consisting of emollients, stabilizing agents, thickening agents, humectants, antimicrobial agents, neutralizing agents, surfactants, water, silicone polymers, alcohols, and hydrogels, anti-inflammatory agents, wound healing agents, as well as additional components as may be known in the art.

Specific, non-limiting examples of additional components which may be comprised in pet care products include the components listed above for personal care products.

4.8 Household/Industrial Products

In a subset of non-limiting embodiments, the present invention provides for household/industrial products comprising a combination of one or more essential oil and/or IC together with one or more fruit acid, as set forth in section 4.4 and 4.5, above.

Non-limiting embodiments of household/industrial products which may utilize the invention include household cleaners such as concentrated liquid cleaners and spray cleaners, cleaning wipes, dish washing liquid, dish washer detergent, spray-mop liquid, furniture polish, indoor paint, outdoor paint, dusting spray, laundry detergent, fabric softener, rug/fabric cleaner, window and glass cleaner, toilet bowl cleaner, liquid/cream cleanser, etc. In a particular embodiment, the invention may be used in a food wash product, designed to clean fruits and vegetables prior to consumption. "Household products" are products, other than personal care products, that would be used by individual consumers. "Industrial products" refers to products that are used in industry.

Household-industrial compositions according to the invention, in addition to one or more essential oil and/or IC together with one or more fruit acid, may further comprise one or (preferably) more than one component selected from the group consisting of surfactants, builders (e.g., sequestering builders, precipitating builders, ion exchange builders), solvents, thickeners, abrasives, acids, bases (alkalis), antimicrobial agents, soaps, bleaching agents, enzymes, preservatives, and sudsing agents, as well as additional components as may be known in the art.

In various non-limiting embodiments of the invention, a household/industrial product comprising a combination of one or more essential oil and/or IC together with one or more fruit acid may further comprise a surfactant, for example, but not limited to, an anionic surfactant such as an alkyl sulfate, an alkyldiphenyloxide disulfonate salt (e.g., the DOWFAX series by the Dow Chemical Company), an alkylbenzenesulfonate, an alcohol ethoxysulfate; a cationic surfactant; a non-ionic surfactant, such as a secondary alcohol ethoxylate (e.g., the TERGITOL series by the Dow Chemical Company) or an alkyl polyglucoside (e.g., the TRITON series by the Dow Chemical Company); or an amphoteric surfactant such as an imidazoline or betaine compound.

In various non-limiting embodiments of the invention, a household/industrial product comprising a combination of one or more essential oil and/or IC together with one or more fruit acid may further comprise a builder, for example, but not limited to, a sequestering builder (chelating agent) such as ethylenediaminetetraacetic acid ("EDTA"), sodium citrate, or a complex phosphate; an ion exchange builder such as zeolite, or a precipitating builder such as sodium carbonate or sodium silicate.

In various non-limiting embodiments of the invention, a household/industrial product comprising a combination of one or more essential oil and/or IC together with one or more fruit acid may further comprise a solvent, for example, but not limited to, water, an alcohol such as methanol, ethanol, isopropyl alcohol, or butanol; a hydrocarbon such as an aromatic hydrocarbon, prolylene glycol, methylene chloride, acetone, a petroleum distillate, and/or a glycol ether.

In various non-limiting embodiments of the invention, a household/industrial product comprising a combination of one or more essential oil and/or IC together with one or more fruit acid may further comprise a thickener, for example, but not limited to, a polyethylene glycol, a methoxypolyethylene glycol, and/or hydroxyethyl cellulose.

In various non-limiting embodiments of the invention, a household/industrial product comprising a combination of one or more essential oil and/or IC together with one or more fruit acid may further comprise an abrasive, such as, but not limited to, silica, feldspar or calcite.

In various non-limiting embodiments of the invention, a household/industrial product comprising a combination of one or more essential oil and/or IC together with one or more fruit acid may further comprise an acid, such as, but not limited to, acetic acid, hydroacetic acid, phosphoric acid or hydrochloric acid.

In various non-limiting embodiments of the invention, a household/industrial product comprising a combination of one or more essential oil and/or IC together with one or more fruit acid may further comprise a base (alkali) such as, but not limited to, ammonia or sodium bicarbonate.

In various non-limiting embodiments of the invention, a household/industrial product comprising a combination of one or more essential oil and/or IC together with one or more fruit acid may further comprise an antimicrobial agent, for example, but not limited to, compounds as set forth above for personal care compositions, and also pine oil and sodium hypochlorite.

In various non-limiting embodiments of the invention, a household/industrial product comprising a combination of one or more essential oil and/or IC together with one or more fruit acid may further comprise a bleaching agent, for example, but not limited to, sodium hypochlorite, hydrogen peroxide, sodium percarbonate and sodium perborate.

In various non-limiting embodiments of the invention, a household/industrial product comprising a combination of one or more essential oil and/or IC together with one or more fruit acid may further comprise an enzyme, such as, but not limited to, a protease or a lipase.

In various non-limiting embodiments of the invention, a household/industrial product comprising a combination of one or more essential oil and/or IC together with one or more fruit acid may further comprise a preservative, such as, but not limited to, butylated hydroxytoluene, glutaraldehyde, and EDTA.

In various non-limiting embodiments of the invention, a household/industrial product comprising a combination of one or more essential oil and/or IC together with one or more fruit acid may further comprise a sudsing agent, such as, but not limited to, diethanolamine or triethanolamine.

In one set of non-limiting embodiments, the present invention provides for surface cleaner compositions comprising (i) one or more EO/IC, preferably where the EO(s)/IC(s) are selected from the group consisting of lemongrass oil and/or an IC thereof; orange oil and/or an IC thereof; cinnamon leaf oil and/or an IC thereof; basil oil and/or an IC thereof; and/or pine oil and/or an IC thereof; at a total concentration of between about 0.1 and 1 percent (weight/weight); a fruit acid, preferably citric acid, at a concentration of between about 1 and 2 percent (weight/weight); (iii) an alcohol, preferably ethanol, at a concentration of between about 5 and 20 percent (weight/weight); and (iv) optionally triclosan at a concentration of between about 0.05 and 1 percent (weight/weight), where the ratio of EO(s)/IC(s) to fruit acid is between about 1:1 to 1:10 (inclusive) and the pH is between about 3 and about 7, preferably between 3 and 5. In certain non-limiting embodiments of the invention, cinnamon leaf oil or an IC thereof and/or pine oil or an IC thereof is not present.

In specific, non-limiting embodiments, the present invention provides for the following surface cleaners, having concentrations of active ingredients as indicated, as well as concentrated stock solutions of these formulations which may be diluted to achieve the respective concentrations:

Surface Disinfectant-LG Cit 2

0.2% Lemongrass oil+2% Citric acid+7.65% alcohol+0.15% surfactants

Surface Disinfectant-LG P Cit 4

0.3% Pine oil+0.1% Lemongrass oil+2% Citric acid+7.45% alcohol+0.15% surfactants Surface Disinfectant-P Cit 5

0.5% Pine oil+2% Citric acid+7.45% alcohol+0.15% surfactants

Surface Disinfectant-PO Cit 7

0.5% Pine oil+0.2% Orange oil+1% Citric acid+5.35% alcohol+0.15% surfactants

Surface Disinfectant-LGO Cit 7

0.5% Lemongrass oil+0.2% Orange oil+1% Citric acid+5.35% alcohol+0.15% surfactants Stock solution of hard surface Disinfectant-LG-O-Cit 1+Dodecanediol:

| Ingredients | % (w/w) |
| --- | --- |
| Lemongrass oil | 3.0 |
| Orange oil | 1.0 |
| Citric Acid | 10.0 |
| 1,12 Dodecanediol | 5.0 |
| SDA 40B alcohol | 79.5 |

-continued

| Ingredients | % (w/w) |
| --- | --- |
| Pluronic Surfactant L-61 | 0.5 |
| Pluronic Surfactant F-127 | 0.5 |
| Pluronic Surfactant F-87 | 0.5 |

Before use this solution is diluted tenfold with water.

Stock solution of hard surface Disinfectant-LG-O-Cit 2+Dodecanediol

| Ingredients | % (w/w) |
| --- | --- |
| Lemongrass oil | 3.0 |
| Orange oil | 1.0 |
| Citric Acid | 20.0 |
| 1,12 Dodecanediol | 5.0 |
| SDA 40B alcohol | 69.5 |
| Pluronic Surfactant L-61 | 0.5 |
| Pluronic Surfactant F-127 | 0.5 |
| Pluronic Surfactant F-87 | 0.5 |

Before use this solution is diluted tenfold with water

The detailed description hereby incorporates, by reference, the specific working examples of the invention set forth below.

The working examples sometimes refer to Softsoap® or Dial® soaps.

Softsoap® is a commercially sold liquid soap comprising water, sodium laureth sulfate, cocamidopropyl betaine, decylglucoside, sodium chloride, fragrance, DMDM hydantoin, PEG-120 methyl glucose dioleate, tetrasodium ethylene diamine tetracetic acid, sodium sulfate, polyquaternium-7, citric acid, poloxamer 124, PEG-7 glyceryl, cocoate, benzophenine-4, and colors.

Dial® soap is a commercially sold liquid soap, where Dial® Antibacterial hand soap comprises, as active agent, 0.15 percent triclosan, and the inactive agents are water, sodium laureth sulfate, ammonium lauryl sulfate, decyl glucoside, cocamidopropyl betaine, glycerine, sodium chloride, PEG-18 glyceryl oleate/cocoate, fragrance, cocamide MEA, DMDM hydantoin, tetrasodium ethylene diamine tetracetic acid and colors.

Example 1

Various concentrations of basil oil and acetic, lactic, and citric acids, separately and in combination, were prepared in 10 percent SDA 40B alcohol and water, and adjusted to 100 percent. Except for citric acid, which was added by weight, all other ingredients were measured by volume. 0.9 ml of each solution were dispensed in sterile culture tubes, in triplicate, and 0.1 ml of a $10^7$ cfu/ml $S.$ $aureus$ culture was added to the tubes, vortexed, and then, five minutes later, 9.0 ml of drug inactivating medium was added to each tube. Serial dilutions were made with the drug inactivating medium. 0.5 ml of the dilutions were plated on trypticase soy agar ("TSA") plates. As a control, water containing 10 percent SDA 40B alcohol was processed in parallel. The plates were incubated at 37° C. for 24-48 hours and then the colony counts were determined. The results are shown in Table 1. The greater synergy was observed between basil oil and citric acid ("CA").

TABLE 1

| Compounds | Log 10 Reduction* |
|---|---|
| 1% Basil oil | 2.7 |
| 0.5% Basil oil | 1.8 |
| 0.25% Basil oil | 0.4 |
| 1% Acetic acid (AA) | 0.2 |
| 1% Lactic acid (LA) | 2.3 |
| 1% Citric acid (CA) | 0.1 |
| 1% Basil oil + 1% LA | 5.4 |
| 1% Basil oil + 1% AA | 3.4 |
| 1% Basil oil + 1% CA | 5.1 |
| 0.5% Basil oil + 1% CA | 5.1 |
| 0.5% Basil oil + 0.5% CA | 5.0 |
| 0.25% Basil oil + 1% CA | 5.0 |

*Log reduction from control bacterial counts ranging from $1 \times 10^6$ to $5 \times 10^6$.

The same methodology was used to test the antimicrobial activity of combinations of citric acid with other essential oils. The results are shown in Table 2. In these experiments, cinnamon oil and citronella oil exhibited superior antimicrobial activities in combination with citric acid.

TABLE 2

| Compounds | Log 10 Reduction* |
|---|---|
| 1% CA | 0.1 |
| 0.5% Cinnamon bark | 2.4 |
| 0.25% Cinnamon bark | 1.1 |
| 0.5% Cinnamon bark + 1% CA | 5.9 |
| 0.25% Cinnamon bark + 1% CA | 4.3 |
| 0.125% Cinnamon bark + 1% CA | 2.6 |
| 0.25% Cinnamon leaf | 2.8 |
| 0.25% Cinnamon leaf + 1% CA | 5.7 |
| 0.125% *Citronella* oil | 1.3 |
| 0.25% *Citronella* oil + 1% CA | 6.2 |
| 0.125% *Citronella* oil + 1% CA | 3.3 |
| 0.25% Orange oil | 0 |
| 0.25% Orange oil + 1% CA | 2.3 |
| 0.25% Lemon oil | 0.05 |
| 0.25% Lemon oil + 1% CA | 3.3 |
| 0.25% Lavender oil | 0.25 |
| 0.25% Lavender oil + 1% CA | 4.0 |
| 0.25% Clove oil | 0.1 |
| 0.25% Clove oil + 1% CA | 3.3 |
| 0.25% Tea tree oil | 0 |
| 0.25% Tea tree oil + 1% CA | 4.7 |
| 0.25% Farnesol | 0 |
| 0.25% Farnesol + 1% CA | 4.0 |

*Log reduction from control bacterial counts ranging from $1 \times 10^6$ to $5 \times 10^6$.

Next, the same general protocol was used to test the efficacy of basil, cinnamon and citronella oils against a variety of organisms, namely *E. coli*, *P. aeruginosa*, MRSA, *C. albicans*, and *S. aureus*. The results, which demonstrate that in these experiments, combinations of cinnamon oil and citric acid exhibited superior antimicrobial action, are shown in Table 3.

TABLE 3

| Compounds | E. coli | P. aeruginosa | MRSA | C. albicans | S. aureus |
|---|---|---|---|---|---|
| 0.25% Basil oil + 1% CA | 6.0 | 5.5 | 5.2 | 1.5 | 5.0 |
| 0.25% Cinnamon bark oil + 1% CA | 6.0 | 6.0 | 5.2 | 4.5 | 4.3 |
| 0.25% *Citronella* oil + 1% CA | 6.4 | 6.4 | 6.5 | 1.0 | 6.3 |
| 0.25% Cinnamon leaf oil + 1% CA | 6.4 | 6.4 | 6.5 | 5.4 | 6.3 |
| 0.25% Eugenol + 1% CA | — | 6.5 | — | 5.5 | — |

*Log reduction from control bacteria counts ranging from $1 \times 10^6$ to $5 \times 10^6$ or *C. albicans* ranging from $1 \times 10^5$ to $5 \times 10^5$.

Example 2

The following experiments were performed to evaluate the effectiveness of a hard surface cleaner composition comprising cinnamon leaf oil and citric acid.

Two stock solutions of a hard surface cleaner/disinfectant was prepared, with the following ingredients (the two solutions contained different amounts of cinnamon leaf oil, and therefore the amount of alcohol to bring the solution to 100% also varied):

| | |
|---|---|
| Cinnamon leaf oil | 3.6 or 7.2% (w/w) |
| Citric acid | 14.3% (w/w) |
| SDA 40B alcohol | 77.2 or 75.49 (w/w) (to bring the volume to 100%) |
| Pluronic surfactant L-61 | 0.7% (w/w) |
| Pluronic surfactant F-127 | 0.7% (w/w) |
| Pluronic surfactant F-87 | 0.7% (w/w) |
| Orange oil | 2.8% (w/w) |

7% of the stock hard disinfectant was diluted with water to 100%.

0.1 ml of culture containing approximately $1 \times 10^7$ colony forming units ("cfu") per milliliter was spread evenly on the surface of $2.5 \times 11$ cm² tiles using a glass rod and left at room temperature for 10 minutes to dry. After 10 minutes 0.3 ml of the diluted surface disinfectant was spread evenly on the tiles with a sterile glass rod and left for another 10 minutes to dry. The tiles were rinsed with 9.6 ml of inactivating medium (BPBNS), which was collected for testing. The collected medium was serially diluted and 0.5 ml was plated onto TSA plates and incubated at 37° C. for 18-24 hours. The colonies on the plates were counted and the values converted to $\log_{10}$. Commercially available Pinesol®, which contains pine oil, was used as a basis for comparison. Pinesol® containing 15% pine oil was diluted with water as per the manufacturer's instructions to a final concentration of 0.9% pine oil. The results are shown in Table 4. The results show that the composition comprising 0.5% cinnamon leaf oil and 1% citric acid exhibited greater antimicrobial activity than the pine oil cleaner against 4 out of 5 microbes tested.

TABLE 4

| Organism | 0.25% cinn. oil + 1% CA | 0.5% cinn. oil + 1% CA | 0.1% Pinesol ® |
|---|---|---|---|
| E. coli | 5.3 | 5.3 | 5.7 |
| P. aeruginosa | 6.1 | 6.1 | 3.9 |
| MRSA | 2.3 | 3.4 | 2.2 |
| C. albicans | 2.5 | 5.2 | 2.1 |
| S. aureus | 3.7 | 4.1 | 2.4 |

*$\log_{10}$ reduction from control bacterial counts ranges from $1 \times 10^6$-$5 \times 10^6$ for all bacteria, but for *C. albicans* counts were $1 \times 10^5$-$5 \times 10^5$.

Example 3

Various concentrations of cinnamon leaf oil and citric acid were dissolved in SDA 40B alcohol (10%) and water, and adjusted to 100 percent. Except for citric acid, which was added by weight, all other ingredients were measured by volume. 0.9 ml of each solution were dispensed in sterile culture tubes, in triplicate, and 0.1 ml of $10^7$ cfu/ml of *S. aureus* culture was added to the tubes, vortexed, and then, five minutes later, 9.0 ml of drug inactivating medium was added to each tube. Serial dilutions were made with the drug inactivating medium. 0.5 ml of the dilutions were plated on trypticase soy agar ("TSA") plates. As a control, water containing 10% percent SDA 40B alcohol was processed in parallel. The plates were incubated at 37° C. for 24-48 hours and then the colony counts were determined. The results are shown in Table 5.

TABLE 5

| Compounds | Log 10 reduction |
|---|---|
| Citric Acid 2% | 0.32 |
| Citric Acid 1.0% | 0.30 |
| Citric Acid 0.5% | 0.20 |
| Citric Acid 0.25% | 0.08 |
| Citric Acid 0.125% | 0.02 |
| Cinnamon leaf oil 0.25% | 0.52 |
| Cinnamon leaf oil 0.5% | 0.55 |
| 0.25% Cinnamon + 0.25% CA | 0.73 |
| 0.25% Cinnamon + 0.5% CA | 3.0 |
| 0.25% Cinnamon + 1.0% CA | 5.6 |
| 0.5% Cinnamon + 0.125% CA | 0.84 |
| 0.5% Cinnamon + 0.25% CA | 2.2 |
| 0.5% Cinnamon + 0.5% CA | 3.2 |
| 0.5% Cinnamon + 1.0% CA | 6.5 |
| 0.5% Cinnamon + 2.0% CA | 6.7 |

Example 4

A liquid soap called "CN1-A" containing cinnamon oil and citric acid was prepared, having the following composition:

| Ingredients | (weight/weight) |
|---|---|
| Deionized water | 59.15% |
| POLYOX N-60K | 0.2% |
| Pluronic F87 Prill | 2.0% |
| UCARE JR-30 | 0.4% |
| DL-Panthenol 50 W | 1.0% |
| Incromine oxide L | 3.0% |
| Crosultane C-50 | 3.0% |
| Montalene C 40 | 3.0% |
| 2-Phenoxy-ethanol | 1.0% |
| Glycerine | 2.0% |
| SD -40B alcohol | 15.5% |
| Cinnamon leaf oil | 0.5% |
| Citric acid | 1.0% |
| Orange oil | 0.2% |
| Distilled water | 7.95% |

To prepare the soap, cinnamon oil, orange oil, citric acid, and phenoxyethanol were dissolved in the alcohol, the remaining ingredients were dissolved in/mixed with water, and then the alcohol and water solutions were mixed. The pH of the mixture was then adjusted to between 5.5 and 6.5 with 0.1 N NaOH.

The antimicrobial activity of the above soap was tested in parallel with commercial Softsoap® containing triclosan (Softsoap® Antibacterial; Colgate-Palmolive). 0.1 ml of a $10^8$ cfu/ml culture of each microbe tested was mixed with 0.1 ml of bovine serum and placed in a sterile culture tube. 0.8 ml of the test soap formulation was added to the tube and vortexed for 30 seconds. Then 9.0 ml DNB was added to neutralize the activity of the soap. The tube was then vortexed and serially diluted with DNB. 0.5 ml of the diluted solution was plated on TSA plates. The same soap base lacking cinnamon oil, citric acid, and orange oil, with phosphate buffered saline mixed with the culture, was used as the control. The results are shown in Table 6.

TABLE 6

| | $Log_{10}$ reduction from control* | |
|---|---|---|
| Organisms | CN-1A | Softsoap ® (0.15% TC) |
| S. aureus | 2.0 | 0.33 |
| P. aeruginosa | 2.5 | 0.6 |
| E. coli | 4.86 | 0.5 |
| MRSA | 2.7 | 0.8 |
| C. albicans | 1.43 | 0.0 |

*$log_{10}$ reduction from control microbe counts which in all cases ranged from $1 \times 10^7$-$5 \times 10^7$.

Example 5

A liquid soap, called "CN1-B" containing cinnamon oil and citric acid was prepared, having the following composition:

| Ingredients | (weight/weight) |
|---|---|
| Deionized water | 63.2% |
| METHOCEL 40-101 | 0.1% |
| Pluronic F87 Prill | 0.1% |
| UCARE JR-30 | 0.1% |
| DL-Panthenol 50 W | 1.0% |
| Incromine oxide L | 3.0% |
| Crosultane C-50 | 3.0% |
| Montalene C 40 | 1.5% |
| 2-Phenoxy-ethanol | 1.0% |
| Glycerine | 2.0% |
| SDA 40B alcohol | 15.5% |
| Cinnamon leaf oil | 0.5% |
| Citric acid | 1.0% |
| Orange oil | 0.2% |
| Distilled water | 7.8% |

To prepare the soap, cinnamon oil, orange oil, citric acid, and phenoxyethanol were dissolved in the alcohol, the remaining ingredients were dissolved in/mixed with water, and then the alcohol and water solutions were mixed. The pH of the mixture was then adjusted to between 5.5 and 6.5 with 0.1 N NaOH.

The antimicrobial activity of the above soap was tested in parallel with commercial Dial® Antibacterial Hand Soap containing triclosan. 0.1 ml of a $10^8$ cfu/ml culture of each microbe tested was mixed with 0.1 ml of bovine serum and placed in a sterile culture tube. 0.8 ml of the test soap formulation was added to the tube and vortexed for 30 seconds. Then 9.0 ml DNB was added to neutralize the activity of the soap. The tube was then vortexed and serially diluted with DNB. 0.5 ml of the diluted solution was plated on TSA plates. The same soap base lacking cinnamon oil, citric acid, and orange oil, with phosphate buffered saline mixed with the culture, was used as the control. The results are shown in Table 7.

TABLE 7

| Organisms | Log$_{10}$ reduction from control * | |
|---|---|---|
| | CN1-B | Dial ® soap (0.15% TC) |
| S. aureus | 5.0 | 0.36 |
| MRSA | 5.1 | 0.03 |
| E. coli | 4.45 | 0 |
| P. aeruginosa | 5.9 | 0.12 |

* log$_{10}$ reduction from control microbe counts which in all cases ranged from $1 \times 10^7$-5 $\times 10^7$ 3.4 $\times 10^6$ for S. aureus, 3-5 $\times 10^6$ for E. coli and 6 $\times 10^5$-1.3 $\times 10^6$ for MRSA.

Example 6

The effectiveness of Softsoap® Juicy Melon (Colgate-Palmolive) with added cinnamon oil, citric acid, and/or triclosan, against MRSA was evaluated. Testing was performed essentially as set forth in the preceding section 9. The results are shown in Table 8.

TABLE 8

| Compounds | Log 10 reduction* |
|---|---|
| Softsoap ® + 1.5% Cin-Cit | 3.63 |
| Softsoap ® + 0.075% TC | 0.15 |
| Softsoap ® + 0.15% TC | 0.20 |
| Softsoap ® + 0.3% TC | 0.58 |
| Softsoap ® + 0.075% TC + 1.5% Cin- Cit | 4.29 |
| Softsoap ® + 0.15% TC + 1.5% Cin-Cit | 4.87 |
| Softsoap ® + 0.3% TC + 1.5% Cin-Cit | 6.38 |

*log$_{10}$ reduction from control microbe counts which in all cases ranged from $1 \times 10^6$-5 $\times 10^6$.

Example 7

The ability of cinnamon oil and citric acid to potentiate the activity of commercial triclosan-containing soaps such as Softsoap® and Dial® Antibacterial Hand Soap containing 0.15% triclosan was tested using an assay essentially as set forth in Section 9, above.

The results are shown in Table 9.

TABLE 9

| | Log$_{10}$ reduction from control * | | |
|---|---|---|---|
| | S. aureus | E. coli | MRSA |
| Softsoap ® -TC | 0.33 | 0.25 | 0.37 |
| Softsoap ® -TC + CIN- Cit | 3.9 | 3.93 | 6.0 |
| Dial ® Soap-TC | 0.36 | 0 | 0.24 |
| Dial ® Soap-TC + Cin-Cit | 3.74 | 4.18 | 6.0 |

* Log reduction from control bacterial counts (ranges from 3-4 $\times 10^6$ for S. aureus, 3-5 $\times 10^6$ for E. coli and 6 $\times 10^5$-1.3 $\times 10^6$ for MRSA.

In these experiments, the combination of cinnamon oil and citric acid was found to substantially improve the antimicrobial activity of the commercial soap.

Example 8

Because a major ingredient of cinnamon oil is eugenol, the effect of adding eugenol on the antimicrobial activity of commercial soaps was also tested. The assay was essentially as set forth in Section 9, above. The results are shown in Table 10.

TABLE 10

| | Log reduction from control * S. aureus |
|---|---|
| Dial ® Soap-TC | 0.30 |
| Dial ® Soap-TC + 0.5% Eugenol + 1% CA | 2.32 |
| Dial ® Soap-TC + 0.5% cinnamon oil + 1% CA | 3.94 |

* Log reduction from control bacterial counts (ranged from 3-4 $\times 10^6$ for S. aureus).

These experiments showed that while adding eugenol improved the antimicrobial effect, the improvement was not as great as that observed for cinnamon oil.

Example 9

The following experiments were performed to evaluate the antibacterial activity of LG and citric acid dissolved in alcohol, where the test organism used was S. aureus. Various amounts of LG oil and citric acid were dissolved in SDA 40B alcohol, and then water was added to result in the EO concentration shown and an alcohol concentration of 10 percent. 0.9 ml of each solution were dispensed in sterile culture tubes, in triplicate, and 0.1 ml of a $10^7$ cfu/ml S. aureus culture was added to the tubes, vortexed, and then, five minutes later, 9.0 ml of drug inactivating medium was added to each tube. Serial dilutions were made with drug inactivating medium. 0.5 ml of the dilutions were plated on trypticase soy agar ("TSA") plates.

As a control, water containing 10 percent SDA 40B alcohol was processed in parallel. The plates were incubated at 37° C. for 24-48 hours and then the colony counts were determined.

The results are shown in Table 11.

TABLE 11

| Compounds | Log 10 reduction from control |
|---|---|
| 1% Citric acid | 0.3 |
| 0.5% LG oil | 1.24 |
| 0.55 LG oil + 1% Citric acid | 5.59 |

*Log 10 reduction from control bacterial counts (control counts ranges from $1 \times 10^6$ to 5 $\times 10^6$)

The results shown in Table 11 indicate that LG oil exhibits superior antibacterial action in combination with citric acid.

Example 10

Soaps were prepared containing one or more essential oil, 1% citric acid, and a soap base containing surfactants, emollients, thickeners etc. The pH range of the soaps was 3.2-3.3.

Soap Containing Lemongrass oil, and Citric Acid (LG-Cit 4) (4 represents total oil 0.4%)

| Ingredients | Percentage (w/w) |
|---|---|
| Deionized water | 63.5 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |

| Ingredients | Percentage (w/w) |
| --- | --- |
| Glycerine | 2.0 |
| SDA 40B | 15.5 |
| Lemongrass oil | 0.4 |

Soap Containing Lemongrass oil and Citric acid (LG-Cit 6)

(6 represents total oil 0.6%)

| Ingredients | Percentage (w/w) |
| --- | --- |
| Deionized water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Lemongrass oil | 0.6 |

Soap Containing Lemongrass oil, Orange oil and Citric acid (LGO-Cit 6)

(6 represents total oil 0.6%)

| Ingredients | Percentage (w/w) |
| --- | --- |
| Deionized water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Lemongrass oil | 0.4 |
| Citric acid | 1.0 |
| Orange oil | 0.2 |

Soap Containing Lemongrass oil, Orange oil and Citric acid (LGO-Cit 7)

(7 represents total oil 0.7%)

| Ingredients | Percentage (w/w) |
| --- | --- |
| Deionized water | 63.2 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |

| Ingredients | Percentage (w/w) |
| --- | --- |
| Lemongrass oil | 0.5 |
| Citric acid | 1.0 |
| Orange oil | 0.2 |

Soap Containing Cinnamon oil, Orange oil and Citric acid (CO-Cit 6)

(6 represents total oil 0.6%)

| Ingredients | Percentage (w/w) |
| --- | --- |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Cinnamon oil | 0.4 |
| Citric acid | 1.0 |
| Orange oil | 0.2 |

Soap Containing Cinnamon oil, Orange oil and Citric acid (CO-Cit 7)

(7 represents total oil 0.7%)

| Ingredient | Percentage (w/w) |
| --- | --- |
| Deionized Water | 63.2 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Cinnamon oil | 0.5 |
| Citric acid | 1.0 |
| Orange oil | 0.2 |

Soap Containing Orange oil and Citric acid (O-Cit 2)

(2 represents total oil 0.2%)

| Ingredients | Percentage (w/w) |
| --- | --- |
| Deionized water | 63.7 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |

-continued

| Ingredients | Percentage (w/w) |
|---|---|
| Glycerine | 2.0 |
| SDA 40B | 15.5 |
| Orange oil | 0.2 |
| Citric acid | 1.0 |

Soap Containing Basil oil (B), Orange oil and Citric acid (BO-Cit 6)
(6 represents total oil 0.6%)

| Ingredients | Percentage (w/w) |
|---|---|
| Deionized water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Basil oil | 0.4 |
| Citric acid | 1.0 |
| Orange oil | 0.2 |

Soap Containing Citronella oil (CR), Orange oil and Citric acid (CRO-Cit 6)
(6 represents total oil 0.6%)

| Ingredients | Percentage (w/w) |
|---|---|
| Deionized water | 63.3 |
| METHOCEL 40-101 | 0.1 |
| Pluronic F87 Prill | 0.1 |
| UCARE JR-30 | 0.1 |
| DL-Panthenol 50 W | 1.0 |
| Incromine Oxide L | 3.0 |
| Crosultane C-50 | 3.0 |
| Montalene C 40 | 1.5 |
| 2-Phenoxy-Ethanol | 1.0 |
| Glycerine | 2.0 |
| SDA 40B | 15.5 |
| Citronella oil | 0.4 |
| Citric acid | 1.0 |
| Orange oil | 0.2 |

Example 11

Certain soaps prepared in Example 14 were tested for antimicrobial activity.

The following method was used. A mixture of 0.1 ml of $10^7$ cfu/ml of S. aureus culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. Softsoap® and Dial® soaps containing 0.15% triclosan was also tested similarly at the same time. The soap base without essential oils and citric acid containing the culture were used as controls. The results, showing 30 second kill activity, are shown in Table 12.

TABLE 12

| Soap | Log 10 reduction from control* |
|---|---|
| LG-Cit 4 | 3.9 |
| LG-Cit 6 | 4.2 |
| O-Cit 2 | 1.5 |
| LOO Cit 6 | 6.4 |

*Log 10 reduction from control bacterial counts (control counts ranges from $1 \times 10^6$ to $5 \times 10^6$)

These data show that when citric acid was used in combination with 0.4% LG oil+0.2% O oil (LGO-Cit 6) superior antibacterial activity was observed as compared to that of the combination of citric acid and LG oil 0.6% (LG-Cit 6) or the additive activity of citric acid+0.4% LG oil (LG-Cit 4) and citric acid+0.2% orange oil (O-Cit 2).

Example 12

Certain soaps described in Example 10 were tested for antimicrobial activity.

The following method was used. A mixture of 0.1 ml of $10^7$ cfu/ml of S. aureus culture and 0.1 ml of bovine serum was placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. Softsoap® and Dial® soaps containing 0.15% triclosan was also tested similarly at the same time. The soap base without essential oils and citric acid containing the culture were used as controls. The results, showing 30 second kill activity, are shown in Table 13.

TABLE 13

| Soap | Log10 reduction from control* |
|---|---|
| LOO-Cit 6 | 6.4 |
| LOO-Cit 7 | 6.5 |
| CO-Cit 6 | 5.1 |
| CO-Cit 7 | 5.2 |
| BO-Cit 6 | 2.87 |
| CRO-Cit 6 | 4.57 |

*Log 10 reduction from control bacterial counts (ranges from $1 \times 10^6$ to $3 \times 10^6$)

These data show that LGO-Cit soaps were found to exhibit higher antibacterial activity compared to the other essential oil/citric acid combination soaps tested.

Example 13

The following experiments were performed to evaluate the antibacterial activity of triclosan, LG oil, and combinations of triclosan (TC) and LG oil.

Patent application WO/2007/077573 by Mukhopadhyay et al. describes an antimicrobial composition containing triclosan and an essential oil where the ratio of triclosan to the essential oil is 1:5 to 1:100 and the preferred ratio range is 1:10 to 1:90. In the example provided in United States Patent Application Publication No. 20050019431 by Modak et al., TC and essential oil at 1:1 ratio showed neither synergistic nor enhanced activity.

Triclosan is often used in personal care products at a concentration of 0.15-0.3%. In order to determine whether or not TC at this concentration would enhance the activity of essential oil at 0.4-0.7% which is the concentration used in various formulations described in this application, the antibacterial activity of soaps containing triclosan, LG oil, or TC and LG oil at TC:LG weight ratios of 1:1.7 to 1:4.6 were evaluated.

To prepare the soaps, TC, LG oil or their combination were dissolved in SDA 40B alcohol and then added to Softsoap® (a formulation lacking triclosan), then diluted with water, where the amount of SDA 40B alcohol used represented 5.5% of the final solution and the amount of Softsoap® used represented 92% of the final solution. Softsoap® was used as the control in this study.

The following method was used. A mixture of 0.1 ml of $10^8$ cfu/ml of *S. aureus* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 14.

TABLE 14

| Soap | Log10 reduction from control* |
| --- | --- |
| Softsoap ® + 0.15% TC | 0.70 |
| Softsoap ® + 0.3% TC | 0.81 |
| Softsoap ® + 0.5% LG oil | 0.76 |
| Softsoap ® + 0.7% LG oil | 0.75 |
| Softsoap ® + 0.15% TC + 0.5% LG oil | 0.74 |
| Softsoap ® + 0.15% TC + 0.7% LG oil | 0.92 |
| Softsoap ® + 0.3% TC + 0.5% LG oil | 0.77 |
| Softsoap ® + 0.3% TC + 0.7% LG oil | 0.77 |

*Log 10 reduction from control bacterial counts (ranges from $5.8 \times 10^7$ to $6.4 \times 10^7$ cfu)

These results indicate that no synergistic or enhanced effect was seen when triclosan was combined with LG oil at weight ratios falling within the range of 1:1.7 to 1:4.6.

Example 14

The antibacterial activity of soaps containing TC-LGO-Cit 6 at weight ratios within the range of between 1:3.3 and 1:4.7 (TC:LG) and between 1:1.4 and 1:2 (LG:Citric acid) were evaluated against *S. aureus*. To prepare the soaps, triclosan/essential oil(s)/citric acid were dissolved in SDA 40 B alcohol and added to Softsoap® (lacking triclosan) and diluted with water, so that the final concentration of alcohol was 5.5% and the final concentration of Softsoap® was 92 percent. A mixture of 0.1 ml of $10^7$ cfu/ml of *S. aureus* culture and 0.1 ml of bovine serum was placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 15.

TABLE 15

| Soap | Log10 reduction from control* |
| --- | --- |
| Softsoap ® | — |
| Softsoap ® + 0.15% TC | 0.24 |
| Softsoap ® + 1% citric acid | 1.49 |
| Softsoap ® + 0.15% TC + 1% citric acid | 2.01 |

TABLE 15-continued

| Soap | Log10 reduction from control* |
| --- | --- |
| Softsoap ® + 0.15% TC + 0.5% LG oil + 1% citric acid | 2.41 |
| Softsoap ® + 0.15% TC + 0.4% LG oil + 0.2% Orange oil + 1% citric acid | 7.93 |

*Log 10 reduction from control bacterial counts (ranges from $1 \times 10^6$ to $5 \times 10^6$ cfu).

The foregoing data show that citric acid was found to enhance the activity of triclosan, and that addition of LG oil+O oil to a combination of triclosan and citric acid further enhanced the effect.

Example 15

The following experiments were performed to compare the antibacterial activity of combinations of (i) lemongrass oil-citric acid+triclosan; (ii) lemongrass oil+citric acid; and cinnamon oil-citric acid+triclosan, all in a Softsoap® base.

To prepare the soaps, triclosan/essential oil/citric acid were dissolved in SDA 40B alcohol and added to Softsoap® (lacking triclosan) and diluted with water, so that the final concentration of alcohol was 5.5% and the final concentration of Softsoap® was 92 percent. A mixture of 0.1 ml of $10^8$ cfu/ml of *S. aureus* culture and 0.1 ml of bovine serum was placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 16.

TABLE 16

| Soap | Log 10 reduction from control* |
| --- | --- |
| Softsoap ® + 0.15% TC | 0.7 |
| Softsoap ® + 0.15% TC + 0.4% LG oil + 0.2% Orange oil + 1% citric acid | 7.93 |
| Softsoap ® + 0.4% LG oil + 0.2% Orange oil + 1% citric acid | 5.73 |
| Softsoap ® + 0.15% TC + 0.4% C oil + 0.2% Orange oil + 1% citric acid | 5.50 |
| Softsoap ® + 0.4% C oil + 0.2% Orange Oil + 1% citric acid | 4.39 |

*Log 10 reduction from control bacterial counts (ranges from $6.4 \times 10^7$ to $9.9 \times 10^7$ cfu)

The above data demonstrate, among other things, that LGO-Cit+Triclosan was found to be more effective than LGO-Cit and CO-Cit+Triclosan.

Example 16

The following experiments were performed to evaluate the effect of adding various essential oil combinations, citric acid (0.5-0.7%), and SDA 40B alcohol (5.5%) to commercial triclosan-containing soaps such as Dial® Soap and Softsoap® containing 0.15% Triclosan ("Dial® Soap-TC" and "Softsoap®-TC" respectively). A mixture of 0.1 ml of $10^8$ cfu/ml of *S. aureus* culture and 0.1 ml of bovine serum were placed in a sterile culture tube. 0.8 ml of the test soap formulation (or phosphate buffered saline as control) was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 17.

Dial® Soap TC-CO-Cit 7

| Ingredients | % W/W |
|---|---|
| Cinnamon oil | 0.5 |
| Orange oil | 0.2 |
| Citric acid | 1.0 |
| SDA 40B alcohol | 5.5 |
| Dial ® Soap-TC | 92.8 |

Dial® Soap TC-LOO-Cit 7

| Ingredients | % W/W |
|---|---|
| Lemongrass oil | 0.5 |
| Orange oil | 0.2 |
| Citric acid | 1.0 |
| SDA 40B alcohol | 5.5 |
| Dial Soap ®-TC | 92.8 |

Dial® Soap TC-LG-Cit 5

| Ingredients | % W/W |
|---|---|
| Lemongrass oil | 0.5 |
| Citric acid | 1.0 |
| SDA 40B alcohol | 5.5 |
| Dial ® Soap-TC | 92.8 |

Softsoap® TC-LGO-Cit 7

| Ingredients | % W/W |
|---|---|
| Lemongrass oil | 0.5 |
| Orange oil | 0.2 |
| Citric acid | 1.0 |
| SDA 40B alcohol | 5.5 |
| Softsoap ®-TC | 92.7 |

TABLE 17

| Soap | Log10 reduction from control* |
|---|---|
| Dial ® Soap TC | 0.36 |
| Dial ® Soap-TC-CO-Cit 7 | 3.9 |
| Dial ® Soap-TC-LG-Cit 5 | 3.35 |
| Dial ® Soap-TC-LGO-Cit 7 | 5.09 |
| Softsoap ®-TC | 0.33 |
| Softsoap ®-TC-LGO-Cit 7 | 4.66 |
| Softsoap ®-TC + 1% citric acid | 2.64 |

*Log reduction from control bacterial counts (ranges from $2.0 \times 10^8$ to $3.5 \times 10^8$ cfu)

The above results indicate that citric acid was found to enhance the activity of soaps containing triclosan; the combination of citric acid and essential oils was found to increase the antimicrobial activity of soap containing triclosan, and superior antimicrobial action was associated with a combination of citric acid, lemongrass and orange oils, and triclosan.

Example 17

The pH of soaps containing 1% citric acid typically ranges between 3.2 and 3.3. To determine whether or not the superior efficacy observed with the combination of essential oils and citric acid is due to the acidic pH, certain EO/citric acid-containing soaps were adjusted to pH 6.0 with 10 N sodium hydroxide and their antibacterial efficacy tested and compared to the corresponding soaps without pH adjustment. For the evaluation of antimicrobial activity, a mixture of 0.1 ml of $10^7$ cfu/ml of S. aureus culture (ATCC #6538) and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 18. ("Softsoap®-TC" is Softsoap® containing 0.15 percent triclosan).

TABLE 18

| Soap | Log10 reduction from control* |
|---|---|
| CO-Cit + Softsoap ®-TC pH 3.25 | 3.9 |
| CO-Cit + Softsoap ®-TC pH 6.0 | 3.25 |
| CLGO-Cit + Softsoap ®-TC pH 3.25 | 5.1 |
| CLGO-Cit + Softsoap ®-TC pH 6.0 | 5.65 |

*Log 10 reduction from control bacterial counts (ranges from $1 \times 10^6$ to $5 \times 10^6$.)

Conclusion: The efficacy was similar at both pH values tested. This indicates that the superior activity of essential oils and citric acid observed is not due to the acidic pH.

Example 18

Household cleansers were prepared comprising citric acid (1-2%), alcohol, and either (i) lemongrass oil; (ii) a combination of lemongrass oil and pine oil; (iii) a combination of lemongrass oil and orange oil; or (iv) a combination of pine oil and orange oil. The antimicrobial effectiveness of these formulations was tested and compared to commercial Pinesol® cleanser (containing 8.7 percent pine oil and other ingredients including detergent and other cleaning agents) as a control.

Stock solution of hard surface Disinfectant-LG-Cit 2:

| Ingredients | % (W/W) |
|---|---|
| Lemongrass oil | 2.0 |
| Citric acid | 20.0 |
| SDA 40B alcohol | 76.5 |
| Pluronic Surfactant L-61 | 0.5 |
| Pluronic Surfactant F-127 | 0.5 |
| Pluronic Surfactant F-87 | 0.5 |

Stock solution of hard surface Disinfectant-LGP-Cit 4

| Ingredients | % W/W |
|---|---|
| Lemongrass oil | 1.0 |
| Pine oil | 3.0 |
| Citric acid | 20.0 |
| SDA 40B alcohol | 74.5 |

-continued

| Ingredients | % W/W |
|---|---|
| Pluronic Surfactant L-61 | 0.5 |
| Pluronic Surfactant F-127 | 0.5 |
| Pluronic Surfactant F-87 | 0.5 |

Stock solution of hard surface Disinfectant-P-Cit 5

| Ingredients | % W/W |
|---|---|
| Pine oil | 5.0 |
| Citric acid | 20.0 |
| SDA 40B alcohol | 73.5 |
| Pluronic Surfactant L-61 | 0.5 |
| Pluronic Surfactant F-127 | 0.5 |
| Pluronic Surfactant F-87 | 0.5 |

After tenfold dilution of each stock solution the disinfectant contained the following percentages (w/w) of each ingredient:
Surface Disinfectant-LG-Cit 2
  0.2% Lemongrass oil+2% Citric acid+7.65% alcohol+0.15% surfactants
Surface Disinfectant-LG-P-Cit 4
  0.36% Pine oil+0.1% Lemongrass oil+2% Citric acid+7.45% alcohol+0.15% Surfactants
Surface Disinfectant-P-Cit 5
  0.5% Pine oil+2% Citric acid+7.45% alcohol+0.15% surfactants.

To prepare the solution of Pinesol® to serve as control, as per the manufacturer's instruction, 6 ml of the Pinesol® containing 8.5% pine oil was diluted to 100 ml. This diluted sample contained 0.52% pine oil.

To test the antimicrobial activity, 0.1 ml of culture containing approximately $1 \times 10^7$ colony forming units ("cfu") of *S. aureus* per milliliter was spread evenly on the surface of $2.5 \times 11$ cm$^2$ tiles using a glass rod and left at room temperature for 10 minutes to dry. After 10 minutes 0.3 ml of the diluted surface disinfectant was spread evenly on the tiles with a sterile glass rod and left for another 10 minutes to dry. The tiles were rinsed with 9.6 ml of inactivating medium (BPBNS), which was collected for testing. The collected medium was serially diluted and 0.5 ml was plated onto TSA plates and incubated at 37° C. for 18-24 hours. The colonies on the plates were counted and the values converted to $\log_{10}$.

TABLE 19

| | Log$_{10}$ reduction from control bacterial counts* | | | |
|---|---|---|---|---|
| Organism | Disinfectant LG-Cit | Disinfectant LGP-Cit | Disinfectant P-Cit | Pinesol |
| *S. aureus* | 3.56 | 1.89 | 0.81 | 2.4 |

*Log 10 reduction from control bacterial counts (ranges from $1 \times 10^6$-$5 \times 10^6$)

These data indicate that a surface cleaner containing 0.2% LG oil and 2.0% citric acid was found to be considerably more effective than a cleaner containing 0.5% pine oil and 2% citric acid as well as commercial Pinesol® Surface cleaner containing 0.52% pine oil. The cleanser containing 0.3% pine oil+0.1% LG oil+2% citric acid was also found to be more effective than the one containing 0.5% pine oil and 2% citric acid.

Example 19

The following stock solution was prepared:
Stock Solution of hard surface Disinfectant-PO-Cit 7

| Ingredient | % W/W |
|---|---|
| Pine oil | 5.0 |
| Orange oil | 2.0 |
| Citric acid | 10 |
| SDA 40B alcohol | 53.5 |
| Pluronic Surfactant L-61 | 0.5 |
| Pluronic Surfactant F-127 | 0.5 |
| Pluronic Surfactant F-87 | 0.5 |

7.2% of the stock hard disinfectant was diluted with water to 100% before use. This diluted samples contained the following concentrations of active ingredients:
Surface Disinfectant-P-Cit 7
  0.5% Pine oil+0.2% Orange oil+1% Citric acid+5.35% alcohol+0.15% Surfactants
The following stock solution was prepared:
Stock Solution of hard surface Disinfectant-LGO-Cit 7

| Ingredient | % W/W |
|---|---|
| Lemongrass oil | 5.0 |
| Orange oil | 2.0 |
| Citric acid | 10 |
| SDA 40B alcohol | 53.5 |
| Pluronic Surfactant L-61 | 0.5 |
| Pluronic Surfactant F-127 | 0.5 |
| Pluronic Surfactant F-87 | 0.5 |

7.2% of the stock hard disinfectant was diluted with water to 100% before use. This diluted samples contained the following concentrations of active ingredients:
Surface Disinfectant-LGO-Cit 7
  0.5% LG oil+0.2% Orange oil+1% Citric acid+5.35% alcohol+0.15% Surfactants
The method used in Example 18 was used to test antimicrobial activity.

TABLE 20

| | S. aureus | P. aeruginosa | E. coli |
|---|---|---|---|
| Log 10 reduction in bacteria-PO-Cit 7 | 0.6 | 5.1 | 5.1 |
| Log 10 reduction in bacteria-LGO-Cit 7 | 5.9 | 4.8 | 5.09 |

*Log$_{10}$ reduction from control bacterial counts (ranges from $1 \times 10^6$-$5 \times 10^6$)

The foregoing data indicate that LGO-Cit is effective against both gram-positive and gram-negative organisms while PO-Cit is not very effective against the gram-positive organism *S. aureus*.

Example 20

The following experiments were carried out using either soap or surface disinfectants containing the EO(s)/citric acid combinations indicated. The test organism used was *Candida albicans*.

Where soap was employed, the following method was used. A mixture of 0.1 ml of $10^7$ cfu/ml of *C. albicans* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results, showing 30 second kill activity, are shown in Table 21.

Where surface disinfectant was employed, the following method was used. 0.1 ml of culture containing approximately $1\times10^7$ colony forming units ("cfu") of *C. albicans* per milliliter was spread evenly on the surface of $2.5\times11$ cm² tiles using a glass rod and left at room temperature for 10 minutes to dry. After 10 minutes 0.3 ml of the diluted surface disinfectant was spread evenly on the tiles with a sterile glass rod and left for another 10 minutes to dry. The tiles were rinsed with 9.6 ml of inactivating medium (BPBNS), which was collected for testing. The collected medium was serially diluted and 0.5 ml was plated onto TSA plates and incubated at 37° C. for 18-24 hours. The colonies on the plates were counted and the values converted to $\log_{10}$.

TABLE 21

| Formulation | Log10 reduction from control* |
|---|---|
| CO-Cit 6 Soap | 1.02 |
| LGO-Cit 6 Soap | 1.27 |
| CO-Cit 7 Surface Disinfectant | 5.2 |
| LGO-Cit 7 Surface Disinfectant | 4.81 |

*Control counts range from $1 \times 10^6$ to $5 \times 10^6$

These results show that CO groups and LGO groups show similar activity against *C. albicans*.

Example 21

Evaluation of the rapid antibacterial activity of various soap formulations was performed as follows.

Method of evaluation of rapidity of kill of soaps. The rapid antimicrobial efficacy of the soaps containing LG and various combinations were tested as follows. A mixture of 0.1 ml of $10^9$ cfu/ml of bacterial cultures and 0.1 ml of bovine serum was placed in a sterile culture tube. 0.8 ml of the test soap formulation was added to the tube and vortexed for 30 seconds. 9.0 ml drug neutralizing fluid (DNF) was added to the tube to neutralize the activity of the soap, this tube was vortexed and serially diluted with DNF. 0.5 ml of the diluted solution was plated on trypticase soy agar plates, incubated at 37° C. for 24-48 hours, and the colony counts were determined. The soap base without essential oils, citric acid, secondary alcohol and Incroquat containing the culture were also tested. PBS was used as the control. LG-O-Cit 5 comprises 0.3 percent (weight/weight) lemongrass oil, 0.3 percent (weight/weight) orange oil, 1.0 percent (weight/weight) citric acid, 1.0 percent (weight/weight) 2-phenoxyethanol and 15 percent (weight/weight) SDA 40B alcohol. LG-O-Cit 4 comprises 0.3 percent (weight/weight) lemongrass oil, 0.1 percent (weight/weight) orange oil, 1.0 percent (weight/weight) citric acid, 1.0 percent (weight/weight) 2-phenoxyethanol and 15 percent (weight/weight) SDA 40B alcohol. The amount of alkanediol, where present, is 0.3 percent (weight/weight). The complete formulations for the soaps specified are set forth in section 4.6, above. The results are shown in Table 22 below.

TABLE 22

Enhancement of the antibacterial activity of LG-0-Cit composition by 0.3% of alkanediols
(Test Organism: *S. aureus*)

| Soap formulations | Log10 reduction from control |
|---|---|
| Base | 1.8 |
| LG-O-Cit 5 | 3.7 |
| 1,2 decanediol (0.3%) | 0.6 |
| LG-O-Cit 5 + 1,2 decanediol | 4.5 |
| LG-O-Cit 4 | 3.6 |
| LG-O-Cit 4 + 1,2 decanediol | 4.8 |
| LG-O-Cit 4 + 1,2 dodecanediol | 4.5 |
| LG-O-Cit 4 + 1,2 Tetradecanediol | 4.5 |

*$\log_{10}$ reduction from control bacterial counts (ranges from $2 \times 10^8$-$5 \times 10^8$)

The results shown in Table 22 indicate that the alkanediols tested enhanced the antibacterial activity of LG+O oil and citric acid disinfectant composition at a concentration of 0.3 percent (weight/weight).

Example 22

The method described in Section 25, above, was used to evaluate the antibacterial activity of soap formulations comprising 0.5 percent of alkanediols. LG-O-Cit 4A comprises 0.3 percent (weight/weight) lemongrass oil, 0.1 percent (weight/weight) orange oil, 1.0 percent (weight/weight) citric acid, 1.0 percent (weight/weight) 2-phenoxyethanol and 17 percent (weight/weight) SDA 40B alcohol. The amount of alkanediol, where present, is 0.5 percent (weight/weight). The complete formulations for the soaps specified are set forth in section 4.6, above. The results are shown in Table 23 below.

TABLE 23

Enhancement of the antibacterial activity of LG-O-Cit A Composition by 0.5% of alkanediols Rapid antimicrobial activity (30 second kill) (Test Organism: *S. aureus*)

| Soap formulations | Log 10 reduction from control |
|---|---|
| Base | 0.8 |
| LG-0-Cit 4A | 4.1 |
| 1,2 decanediol (0.5%) | 1.4 |
| LG-O-Cit 4A + 1,2 decanediol | 6.0 |
| LG-O-Cit 4A + 1,2 dodecanediol | 6.1 |
| LG-O-Cit 4A + 1,12 dodecanediol | 6.0 |
| LG-O-Cit 4A + 1,2 Tetradecanediol | 6.0 |
| LG-O-Cit4A + 0.25% 1,2 decanediol + 0.25% 1,12 Dodecanediol | 6.0 |
| Cn-O-Cit4A | 3.7 |
| Cn-O-Cit4A + 1,2 decanediol | 4.9 |

(pH of all the soaps ranged from 4.5-4.6)
*$\log_{10}$ reduction from control bacterial counts (ranges from $2 \times 10^8$-$5 \times 10^8$)

The results shown in Table 23 indicate that alkanediols at 0.5% concentration showed significant enhancement of the antibacterial activity of LG+O oil+citric acid or Cn+O oil and citric acid disinfectant composition.

Example 23

To evaluate the effect of decanediol on the antibacterial activity of citric acid or citric acid in combination with essential oils, the following experiments were performed. The compounds indicated below were incorporated into Softsoap™ lacking triclosan and the activity was evaluated. Activity was measured as described in Section 25, Example 22. The results are shown in Table 24.

TABLE 24

Rapid antimicrobial activity (30 second kill)
(Test Organism: *S. aureus*)

| Soap formulations (% w/w) | $Log_{10}$ reduction from control |
|---|---|
| Plain Softsoap ® | 0.2 |
| 0.5 decanediol | 1.4 |
| 1.0 citric acid | 1.3 |
| 0.5 decanediol + 1.0 citric acid | 6.5 |
| 0.3 + 0.1 LG – O | 0.1 |
| 0.5 decanediol + 1.0 citric acid + 0.3 + 0.1 LG + O | 7.0 |
| 0.25 decanediol + 0.5 citric acid | 4.7 |
| 0.15 + 0.06 LG + O | 0.1 |
| 0.25 decanediol + 0.5 citric acid + 0.15 + 0.06 LG + O | 5.6 |

*$Log_{10}$ reduction from PBS (control) bacterial counts (ranges from $7 \times 10^7$-$1 \times 10^8$)

The results shown in Table 24 indicate that decanediol and citric acid exhibit synergistic activity, and that further addition of essential oil enhances the activity. The use of decanediol+citric acid+essential oils in soap even at low concentrations was found to show superior antibacterial activity.

Example 24

To determine the effect of LG-O-Cit-1,2 decanediol on the antibacterial activity of triclosan-containing soap, the following experiments were performed.

Dial® soap containing 0.15% triclosan (Dial-T Soap) was used for this test. The following formulation was prepared. The antibacterial activity was then tested using the method set forth in Section 25, Example 21. The results are shown in Table 25.

Dial®-T Soap Containing LG-O-Cit 4 and 0.5% 1,2 decanediol

| Ingredient | Percentage (w/w) |
|---|---|
| Dial ®-T soap | 90.0 |
| SDA 40B | 8.1 |
| Lemongrass oil | 0.3 |
| Orange oil | 0.1 |
| Citric acid | 1.0 |
| 1,2 decanediol | 0.5 |

Original pH was 3.2 pH adjusted to 4.5 with 10.N NaOH

TABLE 25

Enhancement of the activity of Triclosan by LG-0-Cit- 1,2 Decanediol
Rapid antimicrobial activity (30 second kill)
(Test Organism: *S. aureus*)

| Soap formulations | $Log_{10}$ reduction from control |
|---|---|
| Dial ®-T soap | 0.7 |
| Dial ®-T Soap + LG-0-Cit 4 | 5.5 |
| Dial ®-T Soap + LG-O-Cit4- 0.5% 1,2 decanediol | 8.0 |

*$Log_{10}$ reduction from control bacterial counts (ranges from $2 \times 10^8$-$5 \times 10^8$)

The foregoing results indicate that decanediol enhances the activity of Dial®-T Soap+LG-O-Cit 4.

Example 25

The antibacterial activity of LG-O-CitA-D-T lotion, having the following formulation, was tested in a pigskin model.

| Constituent | % (w/w) |
|---|---|
| Water | 65.6 |
| UCARE JR-30M | 0.25 |
| POLYOX WSR-205 | 0.1 |
| Incroquat TMS Behenyl | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerine | 2.0 |
| Allantoin | 0.2 |
| Dimethicone copolyol (Q2-5220) | 2.5 |
| Citric acid | 1.0 |
| 1,2 decanediol | 0.5 |
| Tocopheryl acetate | 0.5 |
| Glyceryl stearate (Arlacel 165) | 1.0 |
| Butylene glycol | 3.0 |
| SDA 40B | 15.0 |
| Lemongrass oil | 0.5 |
| Tea tree oil | 0.5 |
| Orange oil | 0.1 |
| 1,2 Decanediol (SymClairol) | 0.5 |
| Triclosan | 0.3 |

(pH adjusted to 4.5-5.0)

The pigskin model assay was as follows. Six sets of 3×3 $cm^2$ pig skin each mounted on a petriplate were rinsed in 70% isopropanol and air dried. One piece of the pair was contaminated with 30 µl of $10^8$ cfu of MRSA culture; the two pieces were then rubbed against each other for 30 seconds and left at 37° C. to dry for one hour. Three pairs were used for control and another three pairs were used for the test, which was as follows.

To one piece of the pair from the control, 0.1 gm of placebo cream (same as LG-O-Cit4-D (above) without SDA 40B, lemongrass oil, tea tree oil, orange oil, 1,2 decanediol (SymClairol) was applied, rubbed against the other piece for 15 seconds and left at 37° C. for 1 hour. The same procedure was repeated with the test skins in which LG-O-CitA-D-T was applied. Following this, 0.2 ml dilution media (DM) was added to one skin piece and both pieces rubbed again for 15 seconds. The surviving organisms were recovered from the skin by rinsing each piece with 9.9 ml of DM. The washing fluid from both pieces was collected in one petri dish, mixed and transferred to a culture tube from which further serial dilutions were made. Aliquots from the dilutions were plated on TSA plates and incubated for 24-48 hours at 37° C. before colony counts (baseline counts) were determined. The results are shown in Table 26.

TABLE 26

Reduction of Bacterial growth 1 hour post treatment

| Treatment cream | Bacterial counts (cfu/skin) | $Log_{10}$ reduction from control counts |
|---|---|---|
| PBS | $2.2 \times 10^6$ | — |
| Placebo cream (control) | $2.0 \times 10^6$ | — |
| LG-O-Cit A-D-T Lotion | $7.6 \times 10^3$ | 2.37 |

Example 26

The antibacterial activity of preservative compositions was evaluated.

Preservative Composition A

| Ingredients | % (w/w) |
| --- | --- |
| Lemongrass oil | 10 |
| Farnesol | 10 |
| Orange oil | 5 |
| Lactic acid | 7 |
| 1,2 decanediol | 7 |
| SDA 40B alcohol | 61 |

Preservative Composition B

| Ingredients | % (w/w) |
| --- | --- |
| Lemongrass oil | 15 |
| Farnesol | 15 |
| Orange oil | 10 |
| Lactic acid | 10 |
| SDA 40B alcohol | 50 |

Preservative Composition C

| Ingredients | % (w/w) |
| --- | --- |
| Farnesol | 17 |
| Citric acid | 7 |
| 1,2 decanediol | 7 |
| SDA 40B alcohol | 69 |

Preservative Composition D

| Ingredients | % (w/w) |
| --- | --- |
| Lemongrass oil | 15 |
| Orange oil | 5 |
| Lactic acid | 10 |
| 1,2 decanediol | 20 |
| 1,2 Octanediol | 20 |
| SDA 40B alcohol | 30 |

Preservative Composition E

| Ingredients | % (w/w) |
| --- | --- |
| Lemongrass oil | 15 |
| Orange oil | 5 |
| Lactic acid | 10 |
| 1,2 Octanediol | 40 |
| SDA 40B alcohol | 30 |

The pH of these solutions are adjusted to 5.0. 0.5-5.0% of these preservatives can be used in various formulations.

Evaluation of the Preservative efficacy of Composition A and B. The following cream base was prepared to incorporate the preservative before testing.

| Ingredient | Percentage (w/w) |
| --- | --- |
| Water | 70.24 |
| UCARE JR-40 | 0.3 |
| Polawax | 3.0 |
| Incroquat Behenyl TMS | 3.0 |
| Petroleum jelly | 5.0 |
| Stearyl alcohol | 7.0 |
| Propylene glycol | 2.0 |
| Isopropyl myristate | 4.0 |
| Sorbitan oleate | 2.0 |
| Polyoxyl 40 stearate | 2.0 |

An overnight culture of bacteria grown in Trypticase Soy Broth (TSB) was diluted with TSB to obtain $10^8$ CFU organism/ml. For the test samples, 2% of the preservative was added to 10 grams of the cream and mixed well. From this sample, 1 gram aliquots were placed into 10 ml sterile plastic culture tubes and 0.1 ml (100 microliters) of the test inoculum was added and vortexed until uniformly blended. The tubes were then placed into incubators at 37° C. All tubes were incubated for a total of 3 days. At the end of the incubation period 9.0 ml of Butterfield Phosphate Buffered solution with neutralizer was added to the incubated cultured sample and vortexed until completely mixed. The samples were serially diluted and then plated in Trypticase soy agar (TSA). The plates were incubated at 37° C. temperature for 24-48 hours and the counts were read. The results are shown in Table 27, below.

TABLE 27

| | $Log_{10}$ Reduction from control growth | |
| --- | --- | --- |
| | S. aureus | P. aeruginosa |
| Control | — | — |
| Preserv A | 7.8 | 8.0 |
| Preserv B | 6.7 | 4.0 |

*Control growth for S. aureus and P. aeruginosa are $6.5 \times 10^8$ and $1 \times 10^8$ cfu/gm respectively.

Example 27

The following experiments were performed to evaluate wound dressings impregnated with essential oils, citric acid and decanediol.

Antimicrobial Impregnation Solution

| Ingredients | % (w/w) |
| --- | --- |
| Lemongrass oil | 0.3 |
| Orange oil | 0.1 |
| Tea tree oil | 0.5 |
| *Calendula* oil | 0.5 |
| Citric acid | 1.0 |
| Olive oil | 5.0 |
| Propylene glycol | 10 |
| Decanediol | 0.5 |
| SDA 40B alcohol | 51.7 |
| UCARE JR-30 | 0.4 |
| Water | 30.0 |

Antimicrobial/Anti-Inflammatory Impregnation Solution

| Ingredients | % (w/w) |
| --- | --- |
| Lemongrass oil | 0.3 |
| Orange oil | 0.1 |
| Tea tree oil | 0.5 |

-continued

| Ingredients | % (w/w) |
|---|---|
| *Calendula* oil | 0.5 |
| Citric acid | 1.0 |
| Olive oil | 5.0 |
| Propylene glycol | 10 |
| Decanediol | 0.5 |
| SDA 40B alcohol | 51.0 |
| UCARE JR-30 | 0.4 |
| Curcumin | 0.3 |
| Water | 29.7 |

Wound dressings (Dukal non-adherent pads) were dipped into the antimicrobial impregnation solution and dried for 24 hours. The dressings were cut into 1 cm² pieces and the zones of inhibition against various organisms were determined.

Zones of inhibition test. A 1×1 cm² piece of each dressing was placed on a Trypticase soy agar plate seeded on the surface with 0.3 mL of $10^8$ colony forming units (CFU/mL) of the test organism. The plates were incubated at 37° C. for 24 hours. The zone of inhibition around the catheter segments, excluding the diameter of patch, was measured. The results are shown in Table 28.

TABLE 28

| Organism | Zone of inhibition (mm) |
|---|---|
| *S. aureus* | 7.0 |
| MRSA | 8.0 |
| *P. aeruginosa* | 5.0 |
| *C. albicans* | 9.0 |

Various patent and non-patent publications are cited herein, the contents of which are hereby incorporated by reference in their entireties.

We claim:

1. A topical antimicrobial skin disinfectant composition, comprising:
   (i) (a) basil oil at a concentration between about 0.1 and 0.25 percent wt/wt, (b) orange oil at a concentration between about 0.1 and 0.25 percent wt/wt, and (c) lemon oil at a concentration between about 0.1 and 0.5 percent wt/wt;
   (ii) a fruit acid selected from the group consisting of citric acid and lactic acid at a concentration between about 0.125 and 1.0 percent wt/wt;
   (iii) a non-alkanediol alcohol solvent at a concentration between about 5.0 and 20 percent wt/wt selected from the group consisting of ethanol, isopropanol, and combinations thereof; and
   (iv) an alkanediol at a concentration between about 0.3 and 1.0 percent wt/wt selected from the group consisting of octanediol, decanediol, and combinations thereof.

2. The topical antimicrobial skin disinfectant composition of claim 1, further comprising chlorhexidine digluconate at a concentration between about 0.05 and 2.0 percent wt/wt.

3. The topical antimicrobial skin disinfectant composition of claim 1, wherein the fruit acid is citric acid.

4. The topical antimicrobial skin disinfectant composition of claim 1, wherein the topical antimicrobial skin disinfectant composition is formulated as a personal care product selected from the group consisting of a bar soap, a liquid hand soap, a hand sanitizer, a body wash, an acne treatment, a shampoo, a hair conditioner, a cosmetic, a deodorant, a body lotion, a hand cream, a topical cream, an aftershave lotion, a skin toner, a sunscreen lotion, a baby cleansing wipe, and a diaper cream.

5. The topical antimicrobial skin disinfectant composition of claim 1, wherein the composition further comprises one or more than one component selected from the group consisting of emollient, thickening agent, humectant, silicone polymer, and hydrogel.

6. A topical antimicrobial skin disinfectant composition, comprising
   (i) (a) basil oil at a concentration between about 0.1 and 0.25 percent wt/wt, (b) orange oil at a concentration between about 0.1 and 0.25 percent wt/wt, and (c) lemon oil at a concentration between about 0.1 and 0.5 percent wt/wt;
   (ii) a fruit acid selected from the group consisting of citric acid and lactic acid at a concentration between about 0.125 and 2 percent wt/wt;
   (iii) a non-alkanediol alcohol solvent at a concentration between about 5.0 and 20 percent wt/wt; and
   (iv) an alkanediol at a concentration between about 0.3 and 1.0 percent wt/wt, wherein the non-alkanediol of (iii) is an aliphatic alcohol selected from the group consisting of ethanol, isopropanol, and combinations thereof and wherein the alkanediol is selected from the group consisting of: octanediol, 1,2-decanediol, and 1,10-decanediol.

7. The topical antimicrobial skin disinfectant of claim 6, further comprising an aromatic alcohol selected from the group consisting of phenoxyethanol, benzyl alcohol, 1-phenoxy-2-propanol, and phenethyl alcohol or combinations thereof at a concentration between 0.5 and 5 percent wt/wt (weight/weight).

8. The topical antimicrobial skin disinfectant of claim 6, wherein the concentrations of basil oil, orange oil and lemon oil comprise:
   (a) basil oil at a concentration of 0.1 percent wt/wt, orange oil at a concentration of 0.2 percent wt/wt, and lemon oil at a concentration of 0.2 percent wt/wt;
   (b) basil oil at a concentration between about 0.1 and 0.25 percent wt/wt, orange oil at a concentration between about 0.1 and 0.25 percent wt/wt, and lemon oil at a concentration between about 0.1 and 0.5 percent wt/wt; or
   (c) basil oil at a concentration of 0.1 percent wt/wt, orange oil at a concentration of 0.2 percent wt/wt, and lemon oil at a concentration of 0.2 percent wt/wt.

* * * * *